(12) United States Patent
Hegyi et al.

(10) Patent No.: US 12,298,222 B2
(45) Date of Patent: May 13, 2025

(54) LIGHT COLLECTION FROM OBJECTS WITHIN A FLUID COLUMN

(71) Applicant: INGURAN, LLC, Navasota, TX (US)

(72) Inventors: Alex Hegyi, San Francisco, CA (US); Peter Kiesel, Palo Alto, CA (US); Kenneth M. Evans, College Station, TX (US)

(73) Assignee: INGURAN, LLC, Navasota, TX (US)

( * ) Notice: Subject to any disclaimer, the term of this patent is extended or adjusted under 35 U.S.C. 154(b) by 0 days.

(21) Appl. No.: 18/368,994

(22) Filed: Sep. 15, 2023

(65) Prior Publication Data

US 2024/0003803 A1  Jan. 4, 2024

Related U.S. Application Data

(63) Continuation of application No. 17/882,787, filed on Aug. 8, 2022, now Pat. No. 11,796,448, which is a continuation of application No. 17/133,723, filed on Dec. 24, 2020, now Pat. No. 11,442,001, which is a
(Continued)

(51) Int. Cl.
| | |
|---|---|
| *G01N 15/14* | (2024.01) |
| *C12N 5/071* | (2010.01) |
| *G01N 15/10* | (2024.01) |
| *G01N 15/1429* | (2024.01) |

(Continued)

(52) U.S. Cl.
CPC ....... *G01N 15/1459* (2013.01); *C12N 5/0612* (2013.01); *G01N 15/1429* (2013.01); *G01N 15/1434* (2013.01); *G01N 15/1436* (2013.01); *G01N 2015/1006* (2013.01); *G01N 15/149* (2024.01)

(58) Field of Classification Search
CPC .......... G01N 15/1459; G01N 15/1429; G01N 15/1434; G01N 15/1436; G01N 15/149; G01N 2015/1006; C12N 5/0612
See application file for complete search history.

(56) References Cited

U.S. PATENT DOCUMENTS

| | | | |
|---|---|---|---|
| 4,327,972 A | 5/1982 | Brunsting | |
| 4,863,264 A * | 9/1989 | Miyake ............. | G01N 15/1459 250/461.2 |

(Continued)

FOREIGN PATENT DOCUMENTS

| | | |
|---|---|---|
| CN | 102272580 A | 3/2010 |
| CN | 102680379 A | 5/2012 |

(Continued)

OTHER PUBLICATIONS

International Search Report and Written Opinion dated Dec. 2, 2019 issued in related PCT Application No. PCT/US19/49742.
(Continued)

*Primary Examiner* — David P Porta
*Assistant Examiner* — Gisselle M Gutierrez
(74) *Attorney, Agent, or Firm* — Ryan Christensen; Hashim Rahman

(57) ABSTRACT

An optical arrangement receives output light emanating from an object disposed within a fluid column that crosses an optical refraction boundary of the fluid column between the object and the optical arrangement. The optical arrangement modifies the output light such that the modified output light has an intensity that is more uniform than the output light.

10 Claims, 25 Drawing Sheets

Related U.S. Application Data continuation of application No. 16/133,531, filed on Sep. 17, 2018, now Pat. No. 10,908,065.

(51) Int. Cl.
  *G01N 15/1434* (2024.01)
  *G01N 15/149* (2024.01)

(56) References Cited

U.S. PATENT DOCUMENTS

| | | | |
|---|---|---|---|
| 6,159,739 A * | 12/2000 | Weigl | G01N 15/1404 |
| | | | 436/52 |
| 6,473,171 B1 | 10/2002 | Buttry et al. | |
| 6,532,061 B2 * | 3/2003 | Ortyn | G02B 27/0012 |
| | | | 356/28 |
| 7,262,859 B2 * | 8/2007 | Larson | G01N 21/6452 |
| | | | 356/244 |
| 7,416,972 B2 * | 8/2008 | Japp | H01L 23/564 |
| | | | 438/622 |
| 7,616,311 B2 | 11/2009 | Adams et al. | |
| 7,821,631 B1 * | 10/2010 | Javadi | G01N 15/00 |
| | | | 356/244 |
| 8,502,976 B2 | 8/2013 | Sharpe | |
| 8,767,212 B2 | 7/2014 | Kanda et al. | |
| 8,885,153 B2 | 11/2014 | Pittaro et al. | |
| 8,921,098 B2 * | 12/2014 | Gambini | B01L 7/52 |
| | | | 435/286.1 |
| 9,207,066 B2 * | 12/2015 | Martini | G01B 11/046 |
| 9,261,452 B2 * | 2/2016 | Martini | G01N 15/1436 |
| 9,528,925 B2 * | 12/2016 | Kletter | G01N 15/1459 |
| 10,029,283 B2 * | 7/2018 | Deshpande | B01L 3/50273 |
| 10,866,182 B2 | 12/2020 | Marks et al. | |
| 10,908,065 B2 | 2/2021 | Hegyi | C12N 5/0612 |
| 11,598,725 B2 * | 3/2023 | Sinha | G01J 3/14 |
| 11,693,190 B2 * | 7/2023 | Hagen | G02B 6/4246 |
| | | | 385/121 |
| 2003/0058445 A1 | 3/2003 | Fritz | |
| 2006/0072419 A1 | 4/2006 | Tukker | |
| 2007/0146701 A1 * | 6/2007 | Kiesel | G01N 21/05 |
| | | | 250/458.1 |
| 2010/0314557 A1 | 12/2010 | Hayashi | |
| 2011/0176127 A1 | 7/2011 | Masahiko | |
| 2011/0222062 A1 | 9/2011 | Martini et al. | |
| 2012/0085933 A1 * | 4/2012 | Doi | G01N 15/1429 |
| | | | 250/200 |
| 2014/0192359 A1 | 7/2014 | Martini et al. | |
| 2014/0273179 A1 | 9/2014 | Sharpe et al. | |
| 2014/0273192 A1 | 9/2014 | Sharpe et al. | |
| 2015/0211978 A1 | 7/2015 | Durack et al. | |
| 2015/0233704 A1 * | 8/2015 | Martini | G01B 11/0691 |
| | | | 356/635 |
| 2015/0276387 A1 * | 10/2015 | Kletter | G01N 15/1429 |
| | | | 250/226 |
| 2016/0033386 A1 | 2/2016 | Reed et al. | |
| 2017/0016813 A1 | 1/2017 | Wagner | |
| 2018/0038784 A1 | 2/2018 | Marks et al. | |
| 2020/0256781 A1 | 8/2020 | Johnson et al. | |
| 2020/0309664 A1 | 10/2020 | Bahr et al. | |
| 2020/0309671 A1 | 10/2020 | Lin et al. | |
| 2022/0127681 A1 | 4/2022 | Vunjak-Novakovic et al. | |
| 2022/0260494 A1 * | 8/2022 | Sinha | G01J 3/021 |
| 2023/0302451 A1 * | 9/2023 | Hollfelder | B01L 3/502784 |

FOREIGN PATENT DOCUMENTS

| | | |
|---|---|---|
| JP | H08320285 A | 12/1996 |
| JP | 2006250686 A | 3/2005 |
| WO | 2002031182 A1 | 4/2002 |
| WO | 2009069984 A1 | 6/2009 |
| WO | 2013173446 A1 | 11/2013 |
| WO | 2014142924 A1 | 9/2014 |

OTHER PUBLICATIONS

Russian Examination Report and Search Report issued on Nov. 17, 2021 in related RU Appl. No. 2021108163.
Australian Examination Report issued on Nov. 26, 2021 in related AU Appl. No. 2019345236.
Chinese Examination Report and Search Report issued on Mar. 2, 2022 in related CN Appl. No. 201980060330.0.
Japanese Official Action issued on Mar. 17, 2022 in related JP Appl. No. 2021-0514071.
European Extended Search Report issued May 25, 2022 in related EP 19862628.5.
Japanese Official Action issued on Feb. 15, 2023 in related JP Appl. No. 2022-122574.
Korean Official Action issued on Jul. 24, 2023 in related KR Appl. No. 10-2023-7012648.
JS Office Action issued on Dec. 27, 2022 in related U.S. Appl. No. 17/882,787.
European Official Action issued on Dec. 20, 2023 in related EP Appl. No. 19862628.5.
Australian Office Action issued Oct. 23, 2024, in related AU Application No. 2023278127.
Japanese Office Action issued on Jul. 23, 2024, in related JP Application No. 2023-086863.
Korean Office Action issued Jul. 4, 2024, in related KR Application No. 10-2024-719079.

* cited by examiner

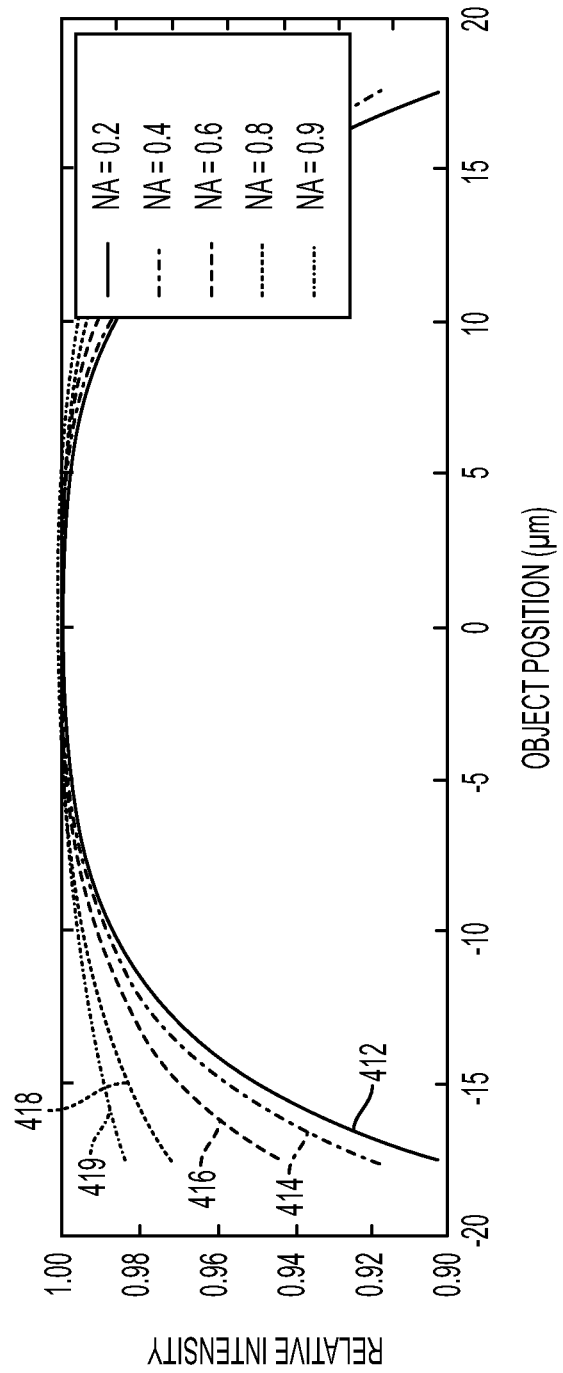

LIGHT COLLECTION FROM OBJECTS WITHIN A FLUID COLUMN

REFERENCE TO RELATED APPLICATIONS

This application is a continuation of U.S. patent application Ser. No. 17/882,787 filed Aug. 8, 2022, which is a continuation of U.S. patent application Ser. No. 17/133,723 filed Dec. 24, 2020, now U.S. Pat. No. 11,442,001, issued Sep. 13 2022, which is a continuation of U.S. patent application Ser. No. 16/133,531 filed Sep. 17, 2018 now U.S. Pat. No. 10,908,065, issued Feb. 2, 2021. The entire disclosures of which are incorporated herein by reference.

BACKGROUND

Object discrimination techniques distinguish between objects of different types. These techniques are particularly useful to sort biological cells according to cell type. Some cell sorting approaches rely on light emanating from the cells to determine their type. In some implementations, cells traveling in a column of fluid are exposed to an excitation light and light emanating from the cells in response to the excitation light is detected. Cells of a first type produce output light that is different in some characteristic, e.g., wavelength and/or intensity, from cells of a second type. The differences in output light emanating from the cells can be the basis for cell type discrimination and sorting.

SUMMARY

Some embodiments are directed to an optical arrangement configured to receive output light emanating from an object disposed within a fluid column. The output light crosses an optical refraction boundary of the fluid column between the object and the optical arrangement. The optical arrangement modifies the output light such that the modified output light has an intensity that is more uniform than an intensity of the output light. For example, within a cross section of the fluid column, the intensity of the modified output light can be substantially uniform irrespective of a position of the object.

According to some embodiments, an optical apparatus includes the optical arrangement and further includes a detector that detects the modified output light and provides an electrical signal responsive to the modified output light.

In accordance with some embodiments, a discrimination system includes an excitation light source configured to generate excitation light and to direct the excitation light toward an object in a fluid column. The object emanates output light in response to the excitation light. The system comprises an optical arrangement configured to receive the output light. The output light crosses an optical refraction boundary of the fluid column between the object and the optical arrangement. The optical arrangement modifies the output light such that the modified output light has an intensity that is more uniform than an intensity of the output light, e.g., the intensity of the modified output light is substantially uniform irrespective of a position of the object in a cross section of the fluid column. An optical detector is configured to detect the modified output light and to provide an electrical signal responsive to the modified output light. Object type discrimination circuitry discriminates between a first type of object and a second type of object based on the electrical signal.

BRIEF DESCRIPTION OF THE DRAWINGS

FIG. 4B provides a family of graphs of the relative intensity of light collected from the fluid column with respect to object position along the x axis for different numerical apertures of the collection optics.

The figures are not necessarily to scale. Like numbers used in the figures refer to like components. However, it will be understood that the use of a number to refer to a component in a given figure is not intended to limit the component in another figure labeled with the same number.

DESCRIPTION

Figure 1A:
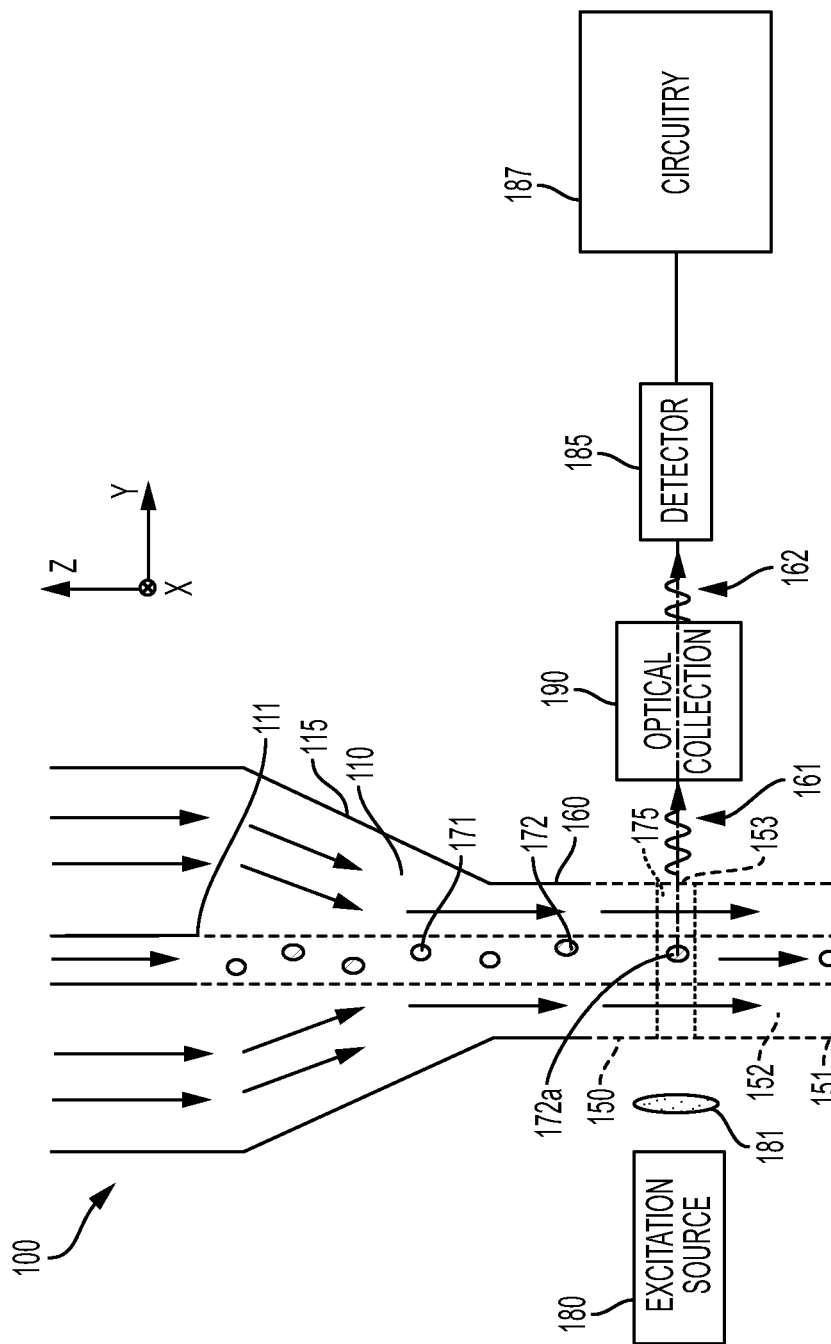
FIG. 1A is a diagram of a system incorporating an optical apparatus in accordance with some embodiments.

Embodiments described herein relate to devices, systems and methods for discriminating between different types of objects. The objects emanate output light in response to an excitation light that is directed toward the objects in a fluid column, such as a flow stream. In some implementations, cell types are distinguished based on the intensity of the output light emanating from the objects. Specific embodiments discussed herein are directed to distinguishing between X chromosome sperm cells and Y chromosome sperm cells. It will be appreciated that the approaches of this disclosure can be applied more generally to distinguishing between any objects of different types so long as the output light emanating from one object type has a discernable difference in at least one characteristic when compared to the light emanating from another object type. In some examples provided, the fluid column is a flow stream that has a curved boundary or interface where refraction of light may occur. For example, the curved boundary of the fluid column may be generally circular in cross section. The fluid column can be bounded by solid walls or may be jetted into the air. The objects may move along the fluid column which may include a central core shaped by a sheath fluid that at least partially surrounds the central core. Light emanating from the objects encounters at least one optical refraction boundary between the objects and other materials, such as at the interface between the fluid column and air.

Due at least in part to the refraction at the fluid-air interface, the light collection efficiency external to the fluid column of light emanating from objects within the column depends upon the position of the objects for systems in the prior art. Light collection efficiency that varies with position is detrimental in applications where the light emanating from the objects must be precisely quantified and such precision is limited by random (not directly observable) position fluctuations of the objects. The approaches disclosed herein enhance the precision of systems that may be limited by such fluctuations, such as jet-in-air flow cytometers. As discussed in more detail below, the positional variability of light intensity collected from objects in a fluid column can be addressed by selectively masking rays at one or more planes (e.g, aperture stop, field stop) of the optical system in order to reduce the dependence of intensity on position.

The approaches outlined herein are particularly applicable to flow cytometry. However, the approaches can be applied to any system where light is collected on one side of an interface from objects emanating the light from the other side of the interface, wherein the interface causes a variation in the emanating light ray paths in a manner dependent on the object's position relative to the detector. Approaches herein modify the light collection efficiency of the output light emanating from the object to compensate for positional variation within the fluid column.

The "jet-in-air" flow cytometer system 100 illustrated schematically in FIG. 1A is one type of flow cytometer that can be used to discuss the concepts of the disclosure. The "jet-in-air" flow cytometer system 100 pumps fluid into a chamber 110 at high pressures causing a flow stream 150 comprising a fluid column to jet out of the exit nozzle 160 of the chamber 110 at high velocity, e.g., about 20 m/s. The fluid column 150 expelled from the exit nozzle 160 can be roughly circular in cross-section and may have a diameter of about 10 µm to about 100 µm in some implementations. The flow stream 150 is composed of a core stream 151 within a sheath stream 152 where the arrows in FIG. 1A indicate the direction of flow of the core and sheath streams 151, 152.

Within the chamber 110, a sample output nozzle 111 ejects the core stream 151 containing objects 171, 172 which may be of multiple types. The core stream 151 is bounded and shaped by a stream 152 of sheath fluid which is ejected from a sheath fluid nozzle (not shown) into the chamber 110. The sheath stream 152 at least partially surrounds the core stream 151, and the sheath stream 152 and the core stream 151 do not substantially mix. The sloping or angled walls 115 of the chamber 110 cause the sheath stream 152 to narrow and/or maintain the cross-sectional size of the core stream 151 within the flow stream 150 before and after the flow stream 150 is ejected from the exit nozzle 160 of the chamber 110. The movement of the sheath stream 152 constrains the objects 171, 172 in the core stream 151 to move toward the center of the flow stream 150 when the fluid column 150 is ejected from the chamber 110. The flow stream 150 delivers the objects 171, 172 to a measurement region 175 of the flow stream 150, e.g., in single file.

As the objects pass through the measurement region 175 of the flow stream 150, light from an excitation light source 180 provides excitation light to the objects 171, 172. The excitation light source 180 can provide light in a broad wavelength band or in a narrow wavelength band. For example, the excitation light source 180 may be a laser. In some configurations, the excitation light may be modified by an optical element 181. For example, the excitation light may be focused on the measurement region 175 by a lens 181. Objects in the measurement region 175 emanate light, e.g., scattered or fluorescent light, in response to the excitation light source 180.

Objects of a first type 171 will emanate light that differs in at least one characteristic in comparison to light that emanates from objects of the second type 172. For example, in some scenarios, objects of the first type 171 will emanate light having a higher intensity than the light that emanates from objects of the second type 172.

An optical collection arrangement 190 is arranged to collect the output light 161 emanating from the object within the measurement region 175 that crosses the optical refraction boundary of the flow stream 150 at the fluid-air interface. The optical arrangement 190 is configured to modify the output light 161 to provide modified output light 162 that compensates for position dependence of the light emanating from the object 172a in the measurement region 175 as discussed in more detail below. A detector 185 receives the modified output light 162 and, in response, generates an electrical signal. In some scenarios, the amplitude of the electrical signal may be different for different object types. The electrical signal is used by discrimination circuitry 187 to distinguish between different types of objects 171, 172. For example, the discrimination circuitry 187 may be configured to compare the amplitude of the electrical signal to a threshold to discriminate between objects of the first type 171 and objects of the second type 172.

Figure 1B:
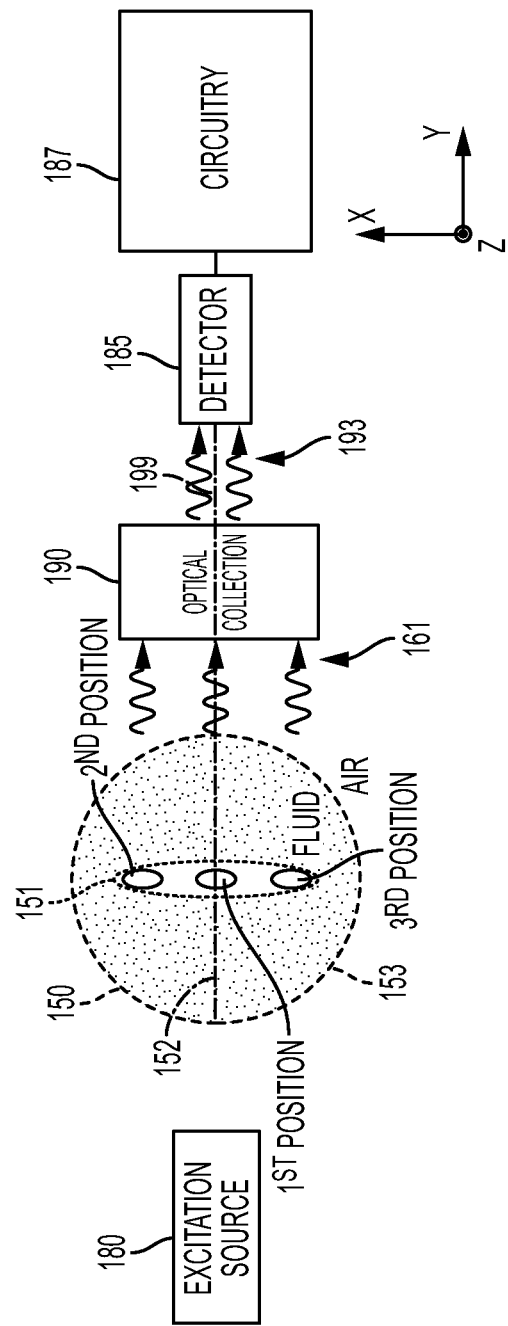
FIG. 1B shows an xy plane cross section of the fluid column in the measurement region of the system of FIG. 1A.

FIG. 1B shows an xy plane cross section of the flow stream 150 in the measurement region 175. In the xy cross section of the measurement region 175, the core stream 151 is elliptical in shape, and the fluid of the core stream 151 comprises at least one object 172a suspended in a buffer solution. The sheath stream 152 is substantially surrounds the core stream 151. In a particular example used for this discussion in this disclosure, the objects 171, 172 are sperm cells and the system 100 is implemented to discriminate X chromosome sperm from Y chromosome sperm.

A focused laser beam generated by the excitation source 180 illuminates the sperm cell 172a within the measurement region 175. The cells 171, 172 are stained with a fluorescent dye, and the excitation light causes the cell 172a within the measurement region to emanate fluorescent output light. The purpose of the elliptical core 151 is to orient a sperm cell 172a such that the flat sides of the sperm cell are facing to the left and the right as shown in FIG. 1B. In this orientation, the flat sides of the sperm cell 172a face the laser 180 and the optical collection arrangement 190, respectively.

When the core stream 151 is elliptical, a sperm cell 172a can take any number of positions along the x-axis within the core stream 151. FIG. 1B shows three possible positions for the sperm cell 172a in the elliptical core 151. In the orientation shown in FIG. 1B, the first possible position for the sperm cell 172a in the core stream 151 is approximately at the center of the elliptical core 151 (on the optical axis 199 of the optical collection arrangement 190), a second possible position is at the top of the core stream 151 (above the optical axis 199), and a third possible position is at the bottom of the core stream 151 (below the optical axis 199). A position-dependent refraction of the output light rays emanating from the sperm cell 172a occurs at the fluid-air interface 153 at the different positions within the core stream 151.

When the sperm cell 172a is located at the first position and the flow stream 150 has a circular cross section as shown in FIG. 1B, the in-plane rays of light emanating from the sperm cell 172a are approximately normally incident on the fluid-air interface 153. Rays that emanate from points of the sperm cell 172a away from its center, or rays that emanate out of the plane of the figure, are not exactly normally incident on the interface 153; these rays are not considered in this simplified discussion, but one of ordinary skill in the art can see how the discussion could be generalized to include them. Thus, no refraction of light occurs at the fluid-air interface 153.

Figure 2A:
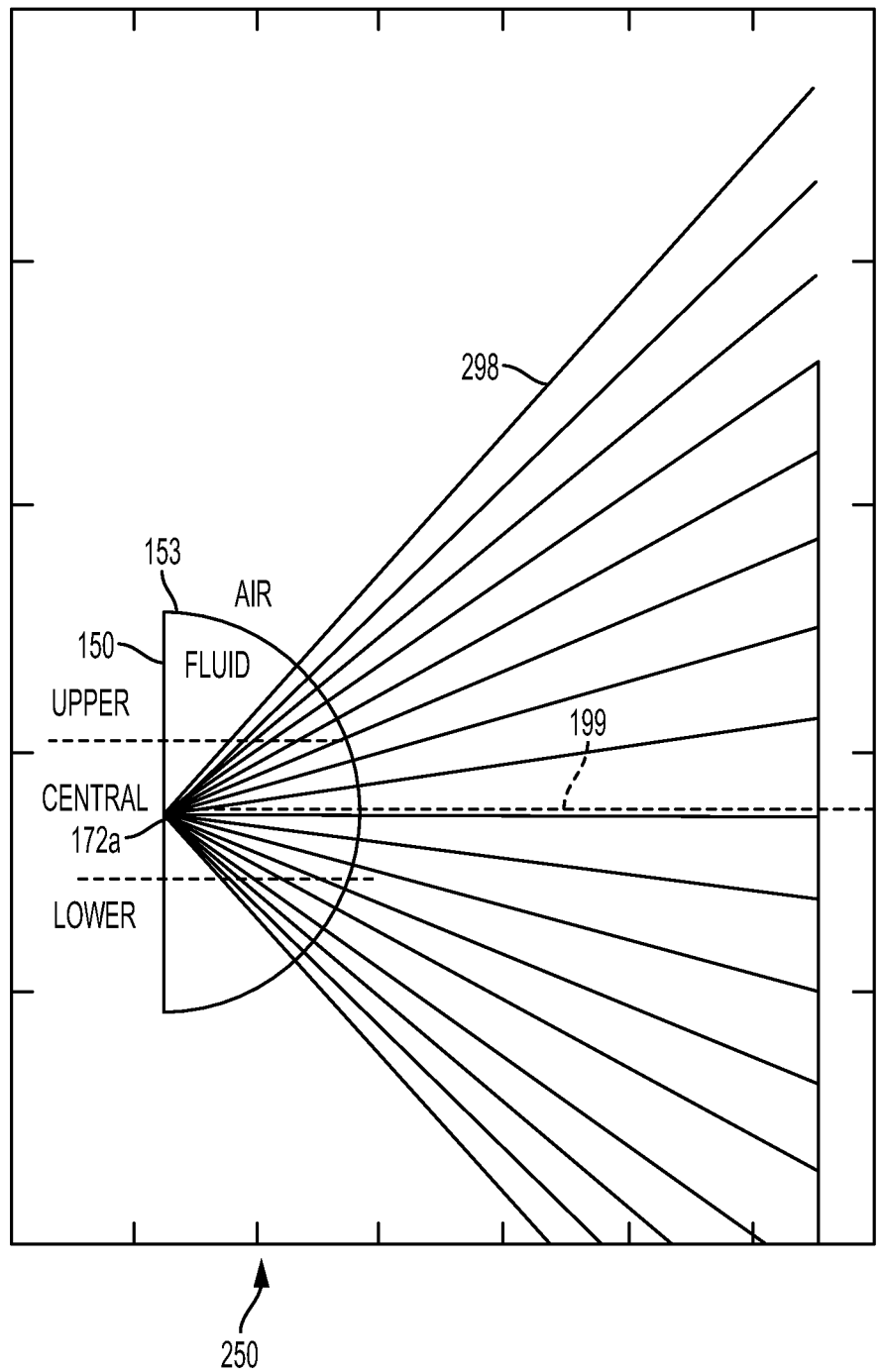
FIG. 2A shows light emanating from an object located near the center of the fluid column with substantially no refraction of light at the fluid-air interface of the fluid column.

The diagram of FIG. 2A shows the absence of light refraction of the output light 298 emanating from a sperm cell 172a and crossing the interface 153 when the sperm cell 172a is at the 1s t position within the elliptical core 151 shown in FIG. 1B. Correspondingly, the in-plane density of the light rays 298 exiting the flow stream 150 in FIG. 2A is uniform with respect to ray angle. Uniform angular density of light rays corresponds to uniform radiance as a function of ray angle.

In contrast, when a sperm cell 172a is off the optical axis 199 and is nearer to the top or bottom of the elliptical core 151, e.g., at the 2n d and 3r d positions of the elliptical core 151 shown in FIG. 1B, at least some of the output rays emanating from the sperm cell 172a encounter the fluid-air interface 153 at an oblique angle. These output rays are refracted at the fluid-air interface 153 in contrast to the normal incidence scenario discussed above. The most oblique rays are the most severely refracted. Refraction of the light rays causes the radiance distribution of the fluorescent light exiting the flow stream 150 across the fluid-air interface 153 to become non-uniform and to vary with position of the cell 172a along the x axis. That is, this refraction changes the radiance distribution of output light emanating from sperm cell 172a outside of the flow stream 150.

Figure 2B:
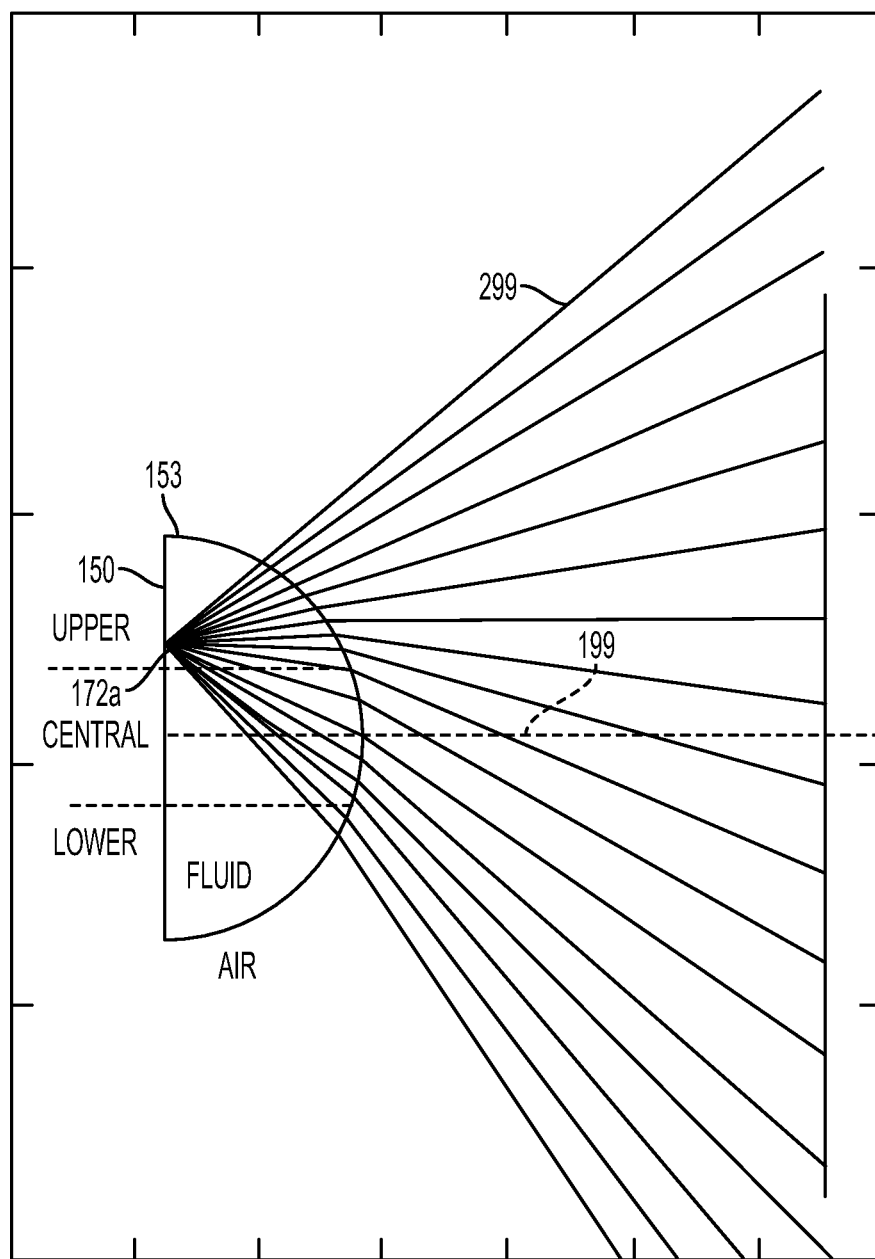
FIG. 2B shows light emanating from an object located in an upper portion of the elliptical core of the fluid column exhibiting refraction of light at the fluid-air interface.

For example, when the cell 172a is located off the optical axis 199, e.g., at the 2n d or 3r d positions shown in FIG. 1B, the density of light rays and thus the radiance on the air side of the interface 153 is higher at positive or negative ray angles, respectively, with respect to the optical axis 199 when compared to the radiance on the air side of the interface 153 at angles parallel to the optical axis 199 or at negative or positive ray angles, respectively. Positive and negative refer to the sign of the ray angle γ in FIG. 3. FIG. 2B is a diagram illustrating light rays 299 emanating from a cell 172a and exiting the flow stream 150 through the fluid-air interface 153 when the cell 172a is located at the 2n d position of the elliptical core 151. In this scenario, the density of light rays, or radiance, at positive ray angles is greater than the density of the light rays parallel to optical axis 199 or at negative ray angles. For an optical system with a predetermined numerical aperture (NA), the amount of light collected by the system from cells of the same type (e.g., the collection efficiency) may vary depending on whether the cell is in the first position or the second position. The positional dependence of the system collection efficiency leads to inaccuracies in determining cell type.

Figure 3:
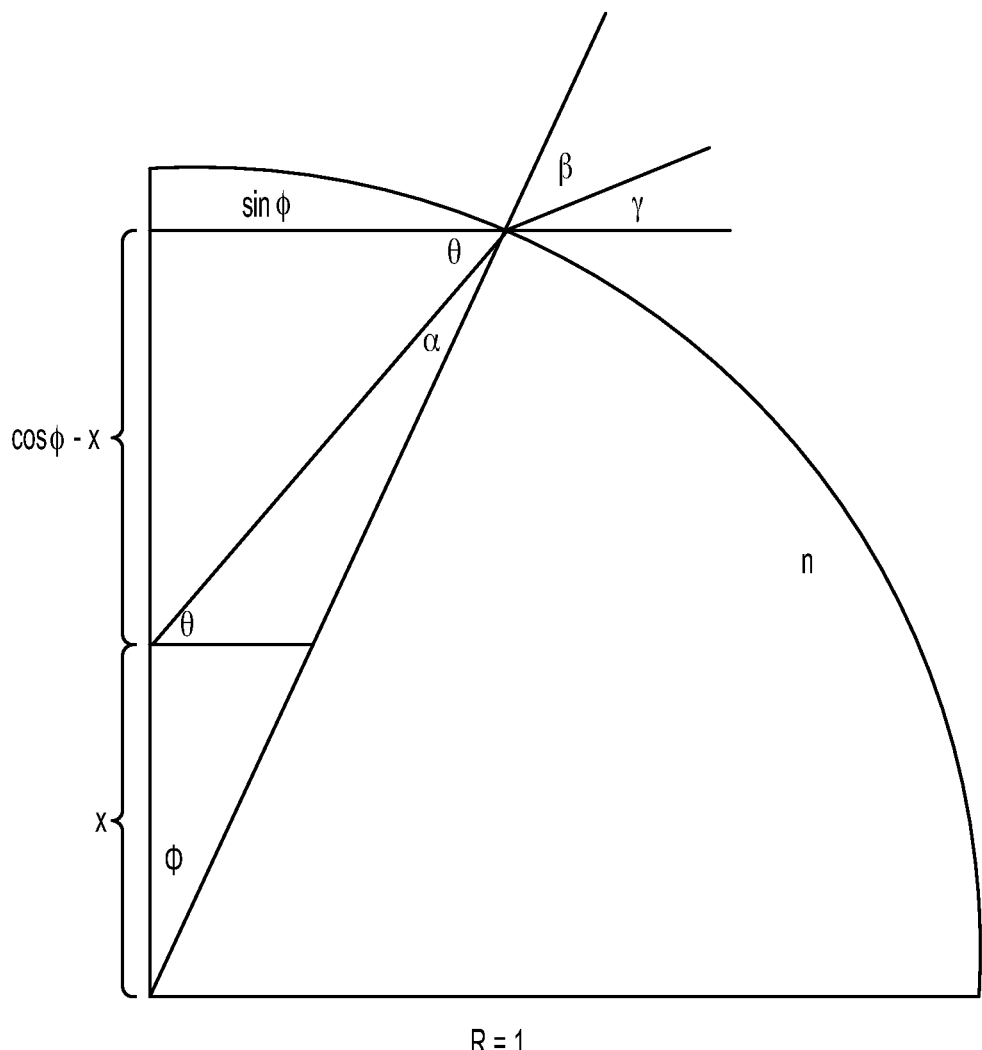
FIG. 3 illustrates development of an analytical formula for angular dependence of the in-plane light ray density as a function of position x.

With reference to FIG. 3, an analytical formula for the light ray density as a function of ray angle γ and sperm position x is determined using Snell's law, where γ is the angle of a light ray, with respect to the optical axis, emanating from the object after refraction at the fluid-air interface. This analysis considers only rays within, or tangential to, the two-dimensional cross-section of the flow stream.

We wish to solve for the density of the light rays with respect to the angle γ, which we can use to determine the density of rays at the entrance pupil of an optical collection system for each sperm position x. This can be written:

$$I_\gamma(\gamma). \tag{1}$$

For our purposes we can assume that the sperm cell emanates light uniformly in all directions, so the density of emanated light rays with respect to the angle θ is:

$$I_\theta(\theta) = 1/\pi, \tag{2}$$

that is, uniformly distributed from $$\theta = -\frac{\pi}{2} \text{ to } \theta = \frac{\pi}{2}.$$

By geometrical analysis:

$$\theta = \tan^{-1}\left(\frac{\cos\phi - x}{\sin\phi}\right); \tag{3}$$

$$\alpha = \pi/2 - \phi - \theta; \text{ and} \tag{4}$$

$$\gamma = \pi/2 - \phi - \beta, \tag{5}$$

wherein the angles γ, θ, φ, α, β, and the distance x are shown in FIG. 3. As the flow stream has index of refraction n, Snell's law yields another relation between the angles:

$$\sin\beta = n \sin\alpha. \tag{6}$$

The density of light rays external to the interface $I_\beta(\beta)$ is related to the density of light rays internal to the interface $I_\alpha(\alpha)$ by the following formula, with $T(\alpha)$ representing the average, across both polarizations, of the transmission through the interface:

$$I_\beta(\beta) = I_\alpha(\alpha)T(\alpha)\left|\frac{d\alpha}{d\beta}\right| \quad (7)$$

The transmission is related to the Fresnel reflection coefficients for s- and p-polarization, $R_s(\alpha)$ and $R_p(\alpha)$, with the following formulas:

$$T(\alpha) = 1 - R(\alpha), \quad (8)$$

$$R(\alpha) = \frac{R_s(\alpha) + R_p(\alpha)}{2}, \quad (9)$$

$$R_s(\alpha) = \left|\frac{\cos\alpha - n\cos\beta}{\cos\alpha + n\cos\beta}\right|^2, \text{ and} \quad (10)$$

$$R_p(\alpha) = \left|\frac{\cos\beta - n\cos\alpha}{\cos\beta + n\cos\alpha}\right|^2. \quad (11)$$

Using Eq. (7) with the above and the following additional relations:

$$I_\phi(\phi) = I_\theta(\theta)\left|\frac{d\theta}{d\phi}\right|, \quad (12)$$

$$I_\alpha(\alpha) = I_\phi(\phi)\left|\frac{d\phi}{d\alpha}\right|, \text{ and} \quad (13)$$

$$I_\gamma(\gamma) = I_\beta(\beta)\left|\frac{d\beta}{d\gamma}\right|, \quad (14)$$

we have an expression for the density of rays with respect to $\gamma$:

$$I_\gamma(\gamma) = I_\theta(\theta)\left|\frac{d\theta}{d\gamma}\right|T(\gamma) \quad (15)$$

Now, the optical collection arrangement's NA is given by the sine of the maximum ray angle $\gamma_0$, so we can solve for this angle in terms of NA:

$$\gamma_0 = \sin^{-1}(NA) \quad (16)$$

Finally, the relative collected light intensity, as a function of sperm position x, is given by integrating Eq. (15) from $-\gamma_0$ to $\gamma_0$ and normalizing by that integral value at x=0:

$$\text{Relative Intensity} = \frac{\int_{-\gamma_0}^{\gamma_0} I_\gamma d\gamma}{\int_{-\gamma_0}^{\gamma_0} I_\gamma(x=0)d\gamma}. \quad (17)$$

Figure 4A:
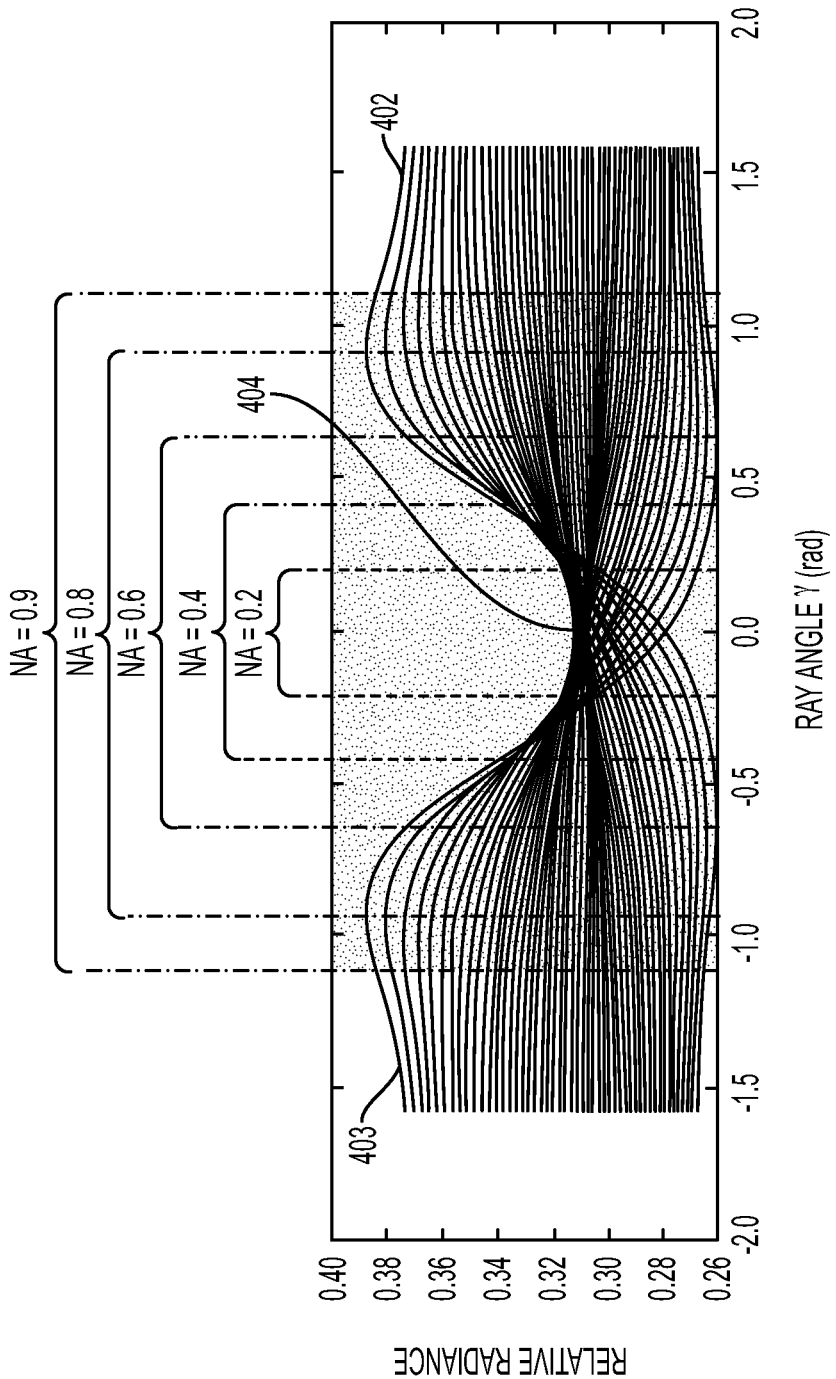
FIG. 4A provides a family of graphs showing the angular dependence of radiance for different object positions.

Using the formula for ray density distribution of Eq. (15), the angular dependence of ray density (radiance) for different sperm positions can be plotted as in FIG. 4A. In FIG. 4A, each of the lines represents the density of rays as a function of angle $\gamma$ for a given sperm position x, where the angle $\gamma$ is in radians. The plots correspond to a series of positions that lie in a range symmetric about x=0, (corresponding to graph 404 in FIG. 4A), which is where the ray density (radiance) is uniform as a function of angle. When x is positive (e.g., $2^{nd}$ position in FIG. 1B, corresponding to graph 402), relative radiance is higher for positive ray angles $\gamma$ and lower for negative ray angles $\gamma$, and the opposite is true when x is negative (e.g., $3^{rd}$ position in FIG. 1B, corresponding to graph 403).

If the numerical aperture of the collection optics (optical collection arrangement 190 in FIGS. 1A and 1B) is large, e.g., approaching one, the variation in collected optical intensity with respect to position for light emanating from an object within the elliptical core is relatively small. This is because essentially all light emanating from the object and directed to the right would be collected by the collection optics, regardless of the exact ray direction, and the total amount of emanating light is invariant to object position (given uniform excitation). In contrast, a small numerical aperture results in a relatively large collected intensity variation with respect to object position, because changes in object position affect the radiance distribution, and a small numerical aperture implies only a portion of this changing radiance distribution is collected. Practical systems may have NAs that are significantly less than one, e.g., less than 0.5, or less than 0.3. The family of graphs provided in FIG. 4B illustrates the relative intensity of light collected from an object, as a function of object position x, through collection optics with different NAs. FIG. 4A illustrates the range of angles $\gamma$ captured by the different numerical apertures of FIG. 4B.

In the family of graphs of FIG. 4B, graph 412 shows the relative intensity with respect to position along the x axis for collection optics (e.g., optical collection arrangement 190 shown in FIGS. 1A and 1B) having a numerical aperture (NA) of 0.2; graph 414 shows the relative intensity with respect to position along the x axis for collection optics having an NA of 0.4; graph 416 shows the relative intensity with respect to position along the x axis for collection optics having an NA of 0.6; graph 418 shows the relative intensity with respect to position along the x axis for collection optics having an NA of 0.8; and graph 419 shows the relative intensity with respect to position along the x axis for collection optics having an NA of 0.9. It is clear from FIGS. 4A and 4B that collection optics having smaller NAs produce a larger variation in collected light intensity with respect to object position when compared to collection optics having larger NAs. Additionally, collection optics with larger NAs collect light rays having a wider range of refraction angles than collection optics having smaller NAs, and therefore have a higher overall collection efficiency.

Various embodiments disclosed herein are directed to collection devices (e.g., arrangement 190 shown in FIGS. 1A and 1B) that reduce the variation in collected light intensity with respect to object position in a flow stream. Some embodiments discussed herein can provide modified output light that has less than about a 3%, or less than about a 2%, or even less than about a 1% measured intensity variation for a deviation in position of the object that is less than 60% of a radius of the flow stream away from a center of the flow stream along an axis perpendicular to the optical axis. Many applications are sensitive to intensity measurement errors, which may arise from a variety of sources. Due to the difficulty in reducing intensity fluctuations by precisely controlling the position of objects within the flow stream, it is useful to instead reduce the variation in collected light intensity with respect to object position by careful design of the optical collection arrangement. For applications such as X/Y sperm sorting, it is often the case that two or more cell populations are to be separated based on the difference in measured fluorescence intensity between the populations. If the random position fluctuations lead to fluctuations in collected light intensity that are greater in magnitude than the nominal difference in fluorescence intensity of the two populations, it is not possible to distinguish them with simultaneously high yield and high purity. The fluorescence intensity difference between X and Y sperm cells is typically only a few percent (e.g., ~4% for bovine sperm). Current sperm sorter systems can in theory achieve high throughput by increasing the flow rate of the core stream, but this has the effect of increasing the width of the core stream. Consequently, there would be a large uncertainty of the sperm position within the core of the flow stream. This position uncertainty and the resultant fluctuations in collected fluorescence intensity limit the maximum throughput of current sperm sorter systems to levels which do not obscure the small fluorescence intensity difference between X and Y sperm.

In sperm sorter applications, the sperm cells may be stained with Hoechst 33342 (Ho33342), a cell-permeable dye that enters the cell nuclei and binds selectively to A-T base pairs in the minor groove of double-stranded DNA within the sperm head of live cells. Typically, a UV laser is used to excite the stained sperm cells. When excited optically (at or near 350 nm), Ho33342 stained Y-chromosome bearing (male) and X-chromosome bearing (female) sperm can be resolved by measuring a small difference in total fluorescence from each cell. The difference in total fluorescence is proportional to the amount of stain within the sperm cell, which is proportional to the chromosomal content. This difference varies between mammalian species, but in domestic animals it is on the order of 4%.

One approach for intensity—position compensation is evident in FIGS. 4A and 4B. The brackets in FIG. 4A highlight regions of integration that correspond to fluorescence collection optics with a given NA. Graphs of the collected intensity variation with respect to object position for the NAs of FIG. 4A are provided in FIG. 4B. In FIG. 4B, for a given NA, integration over the fluorescence collection region is performed such that the intensity of collected light can be plotted as a function of each sperm position. It is evident from FIG. 4B that increasing the NA of the collection optics helps to decrease the influence of object position on the fluorescence intensity gathered via the collection optics.

Embodiments described herein relate to collection optics (e.g., the optical collection arrangement 190 in FIGS. 1A and 1B) that reduce collected light intensity variation with respect to object position as described above. According to some embodiments, the collection optics operate by masking rays in "angle space", that is, the collection optics selectively collect, attenuate, and/or block rays from different angles $\gamma$ in order to achieve a desired intensity vs. position profile. In practice, an "angle space" masking function can be applied at a pupil (e.g., entrance pupil, exit pupil, or aperture stop) of an optical system, where the position of a ray intersection with the pupil plane corresponds to the angle $\gamma$. In some embodiments, the collection optical arrangement achieves a desired, e.g., flatter, intensity vs. position profile by preferentially collecting higher angle (pointing away from the optical axis) light rays over lower angle light rays.

Figure 5A:
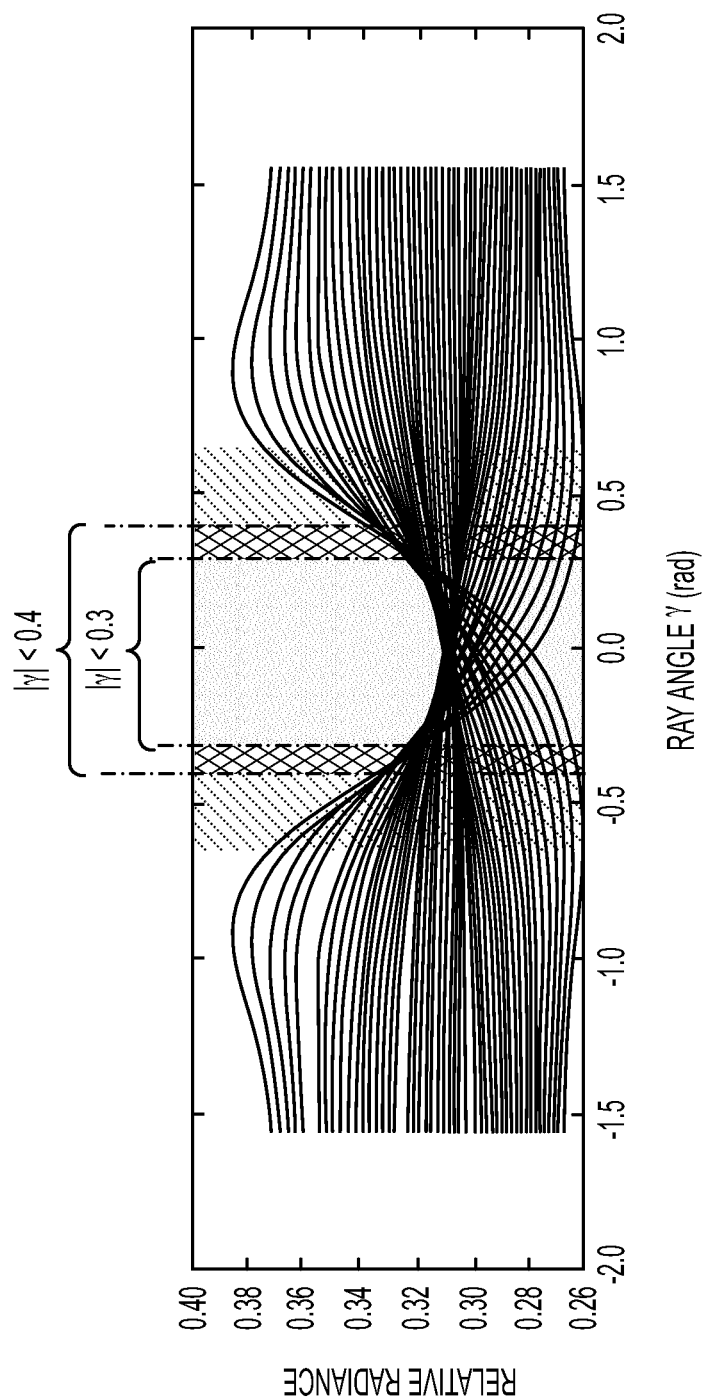
FIG. 5A provides a family of graphs of the angular dependence of radiance for different positions of the object and showing regions of exclusion.
Figure 5B:
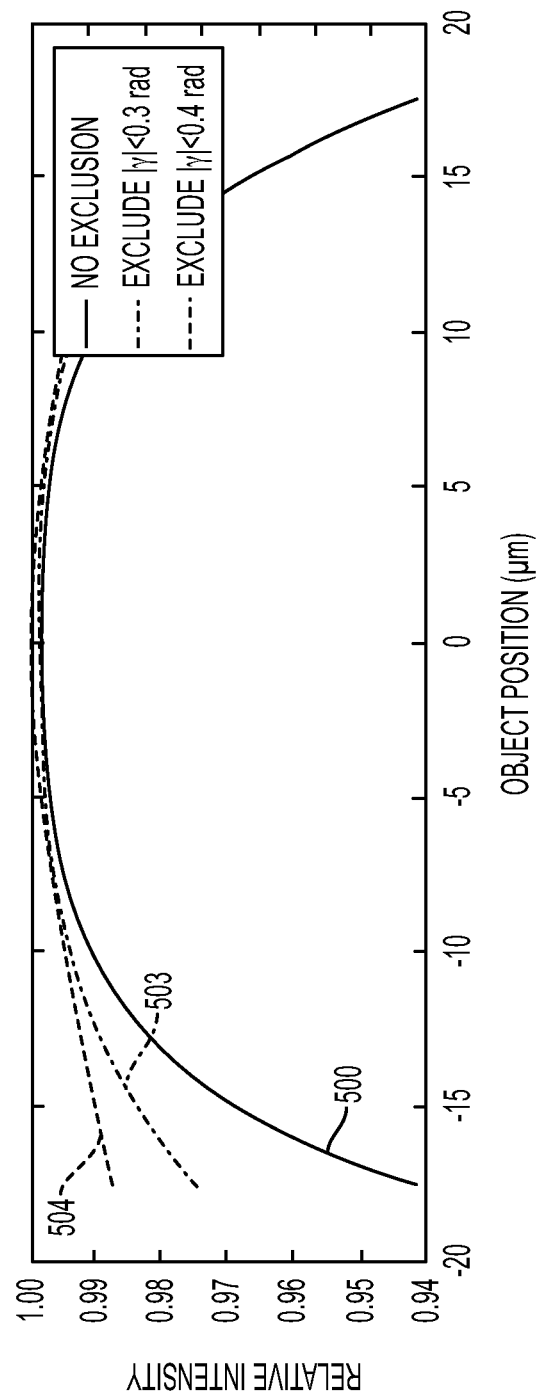
FIG. 5B shows the relative intensity of light collected from the fluid column with respect to object position along the x axis when no angles are excluded, when rays having angles between −0.3 rad and +0.3 rad are excluded, and when rays having angles between −0.4 rad and +0.4 rad are excluded.

FIGS. 5A and 5B illustrate how excluding low-angle refracted rays, at a given NA, causes the intensity-vs-position curve to flatten out. Excluding the low angle rays excludes the rays that produce the most variation in the intensity vs. position profile, whereas the angular variation of radiance at high positive angles tends to cancel the corresponding variation at high negative angles. FIG. 5A shows plots of the relative radiance vs. ray angle, $\gamma$, for different positions of the object along the x axis where the angle $\gamma$ is in radians. In FIG. 5A, each graph corresponds to an object position, x, within the core of a flow stream, as indicated in FIG. 3. The brackets in FIG. 5A show the portion of the light rays that will be excluded by the collection optics for each position x, when rays having angle magnitude less than 0.3 rad are excluded (bottom bracket in FIG. 5A) and when rays having angle magnitude less than 0.4 rad are excluded (top bracket in FIG. 5A).

FIG. 5B shows the relative collected light intensity vs. position of the object along the x axis when no angles are excluded (graph 500), when rays having angles between −0.3 rad and +0.3 rad are excluded (graph 503) and when rays having angles between −0.4 rad and +0.4 rad are excluded (graph 504). Graph 5B shows that when lower angle rays are excluded, the relative intensity vs. position graph exhibits less intensity variation with respect to position.

Figure 6:
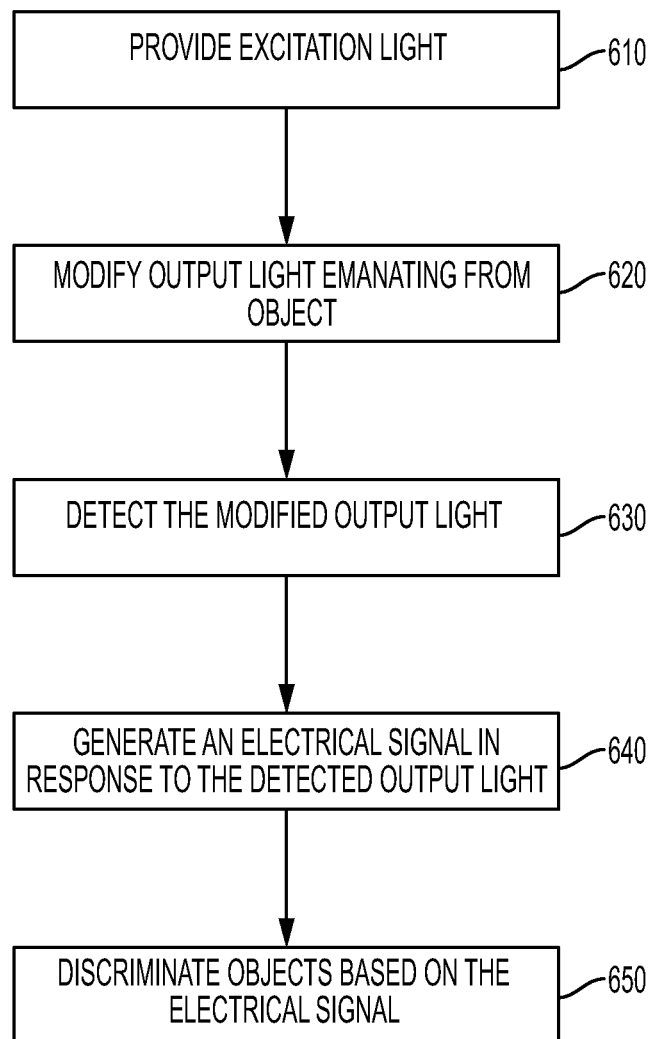
FIG. 6 is a flow diagram of an approach for identifying objects traveling in a fluid column with reduced positional variation of detected output light in accordance with some embodiments.

An approach for identifying objects traveling in a fluid column in the presence of positional variation is illustrated in the flow diagram of FIG. 6. The process includes modifying 620 output light emanating from the object passing through a cross section of a flow stream such that an intensity of the modified output light is more uniform than the intensity of the unmodified output light. In some embodiments, the modified output light is substantially uniform irrespective of a position of the object. The modified output light is detected 630 and an electrical signal is generated 640 in response to the detected modified output light. A processor or other circuitry may use the electrical signal to discriminate 650 between objects of different types. For example, the circuitry may compare the amplitude of the electrical signal (which corresponds to the intensity of the detected light) to a threshold value to discriminate between objects of a first type and objects of a second type. Optionally, in some implementations, excitation light may be generated 610 by an excitation source and directed to the cross section of the flow stream wherein the object emanates the output light in response to the excitation light.

Figure 7:
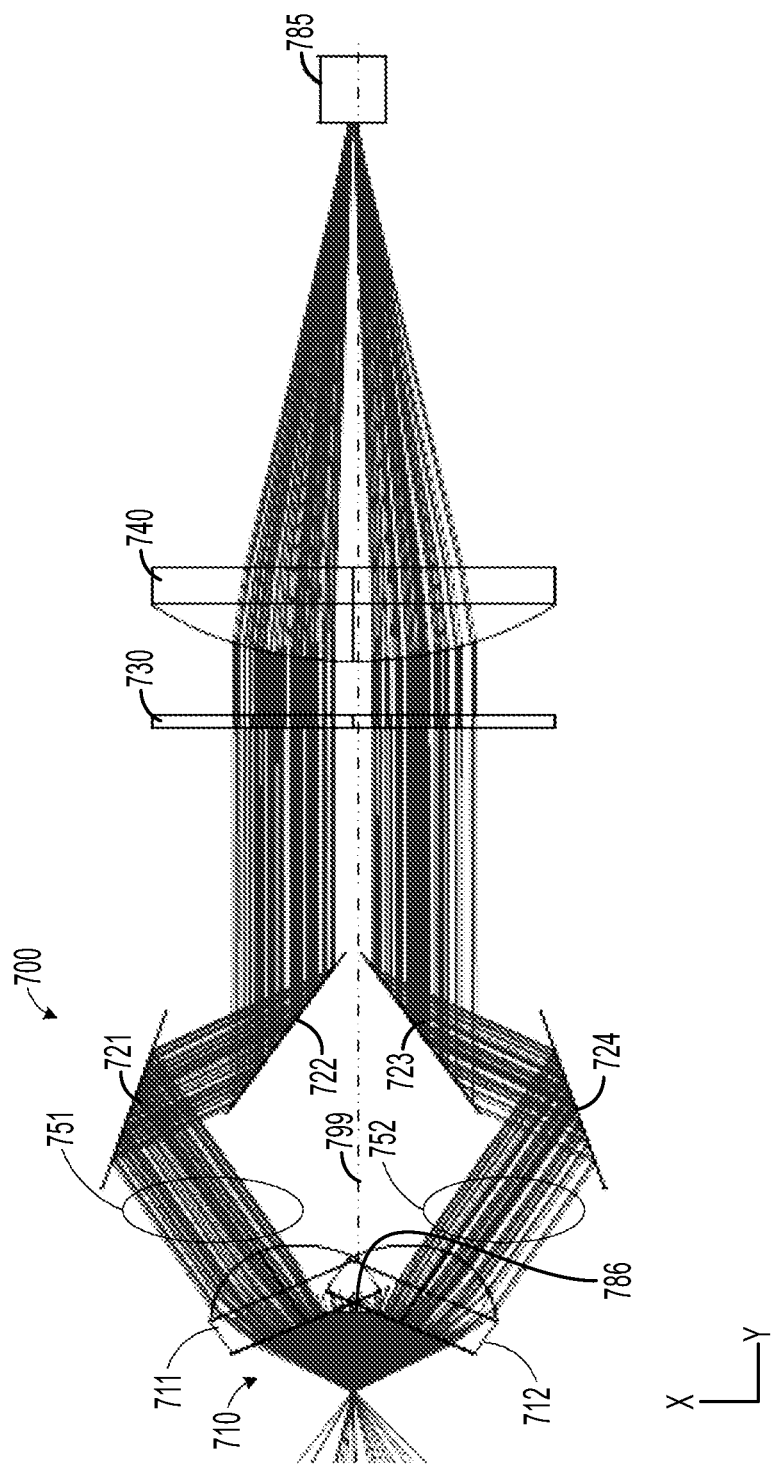
FIG. 7 is a top view of a ray tracing simulation of an optical system that includes an optical apparatus in accordance with some embodiments.

FIG. 7 is a top view of a ray tracing simulation of an optical system 700 that includes an optical apparatus 710 in accordance with some embodiments. Apparatus 710 effectively extends the NA of the collection optics in the plane of a cross section of a fluid column, preferentially collecting higher angle rays that are more balanced in terms of position vs. intensity over lower-angle rays that tend to inject variation into the position vs. intensity profile, as explained in the discussion of FIGS. 5A and 5B. Optical collection arrangement 710 modifies light emanating from an object in a cross section of a flow stream such that an intensity of the modified output light is more uniform than the output light emanating from the object. The modified output light can be substantially uniform irrespective of a position of the object within the cross section. In this particular embodiment, the intensity of the modified output light is substantially uniform irrespective to the position of the object along an axis perpendicular to an optical axis of the collection arrangement. Other embodiments may cause an intensity of the modified output light to be substantially uniform independent of a position of the object along another axis, such as the optical axis of the collection arrangement.

The optical collection arrangement 710 preferentially collects light rays emanating from the object at higher angles with respect to the optical axis 799 of the optical arrangement over light rays emanating from the object at lower angles with respect to the optical axis 799. In some implementations, the optical collection arrangement 710 is a split objective lens. A first section 711 of the split objective lens 710 collects a first portion 751 of the higher angle light emanating from the object (object not shown in FIG. 7). A second section 712 of the split objective lens 710 collects a second portion 752 of the higher angle light emanating from the object. As shown in FIG. 7, in some embodiments, a mask that further prevents the collection of lower angle rays may be disposed anywhere that the lower angle rays would be blocked, e.g., near an aperture stop or pupil plane, where the light is collimated. For example, a mask 786 may be disposed between the two lenses 711, 712 as shown in FIG. 7.

As indicated in FIG. 7, the system 700 may be implemented as a folded optical system using mirrors 721, 722, 723, 724 to redirect the collected portions of light along the optical axis 799 of the system 700 and toward the detector 785. Mirrors 721, 722 redirect the first portion 751 of light toward and along the optical axis and mirrors 723, 724 redirect the second portion 752 of light toward and along the optical axis 799. As illustrated in FIG. 7, the system 700 may optionally include a filter 730 such as an optical bandpass or longpass filter configured to substantially attenuate the excitation light. The system 700 can include lens 740 configured to focus the first and second portions 751, 752 of the light toward the detector 785.

Figure 8:
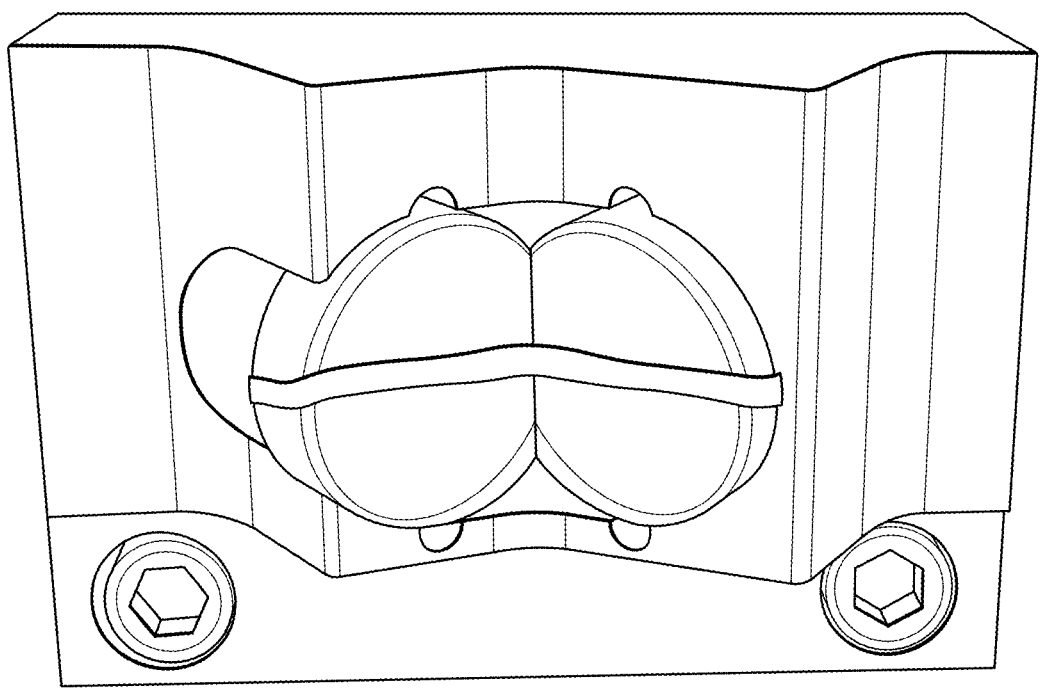
FIG. 8 is a photograph of a split objective lens configured to reduce the positional variation of detected output light for objects in a fluid column in accordance with some embodiments.

FIG. 8 is a photograph of a split objective lens configured to reduce the variation of intensity with respect to object position. It should be noted that the split-objective design allows the fluorescence collection optics to be placed closer to the flow stream than would otherwise be possible, due to the spatial obstruction caused by the nozzle generating the flow stream. A single lens with the same effective NA as the split objective would be too big to place its focal point immediately below the nozzle generating the flow stream. The optical detection of objects within the flow stream is optimally performed immediately after the flow stream exits the nozzle, where the stream is most stable, therefore it is important to have high NA optics that do not interfere with the nozzle.

Figure 9A:
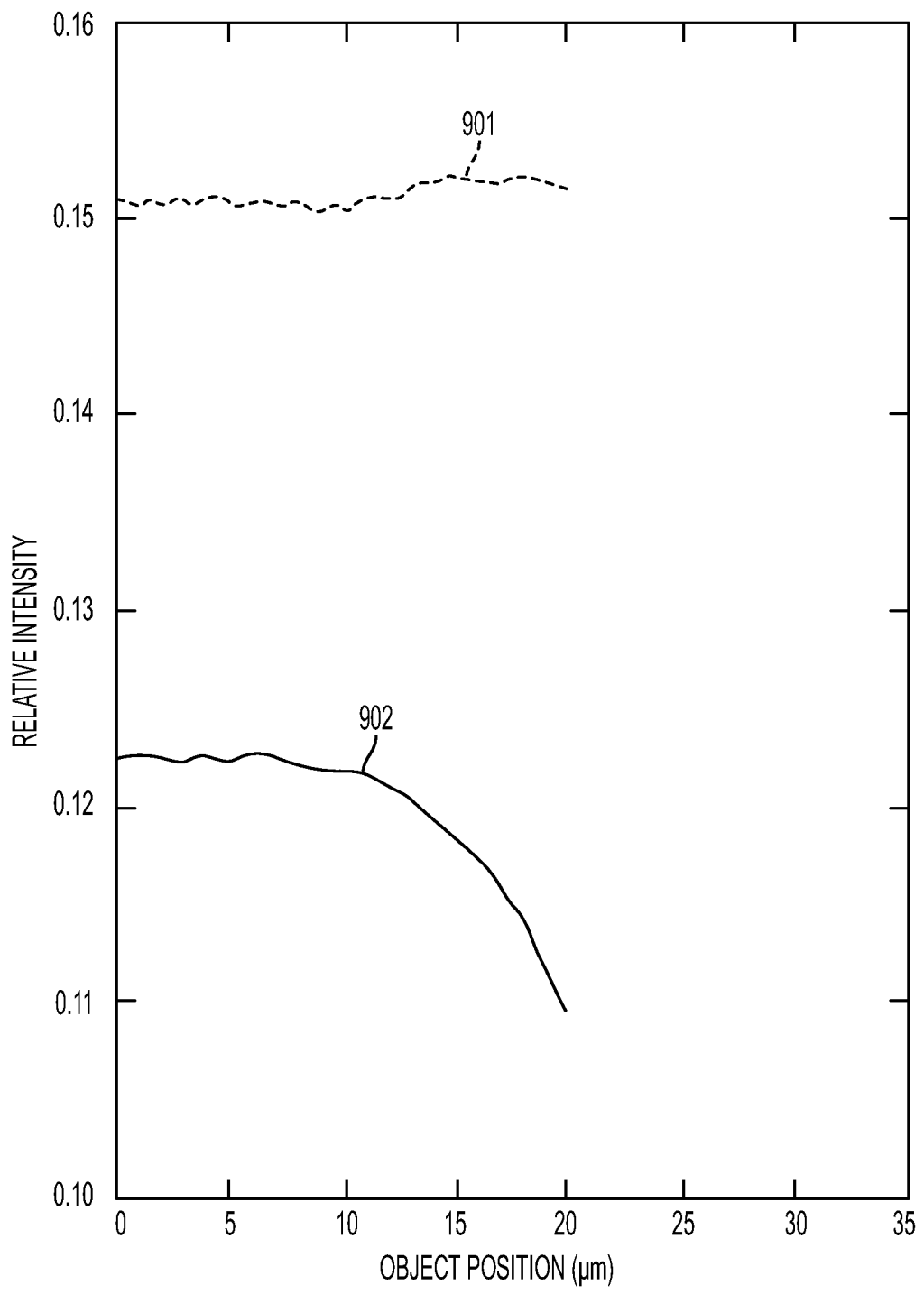
FIGS. 9A and 9B illustrate the simulated performance of the optical apparatus of FIG. 7.
Figure 10:
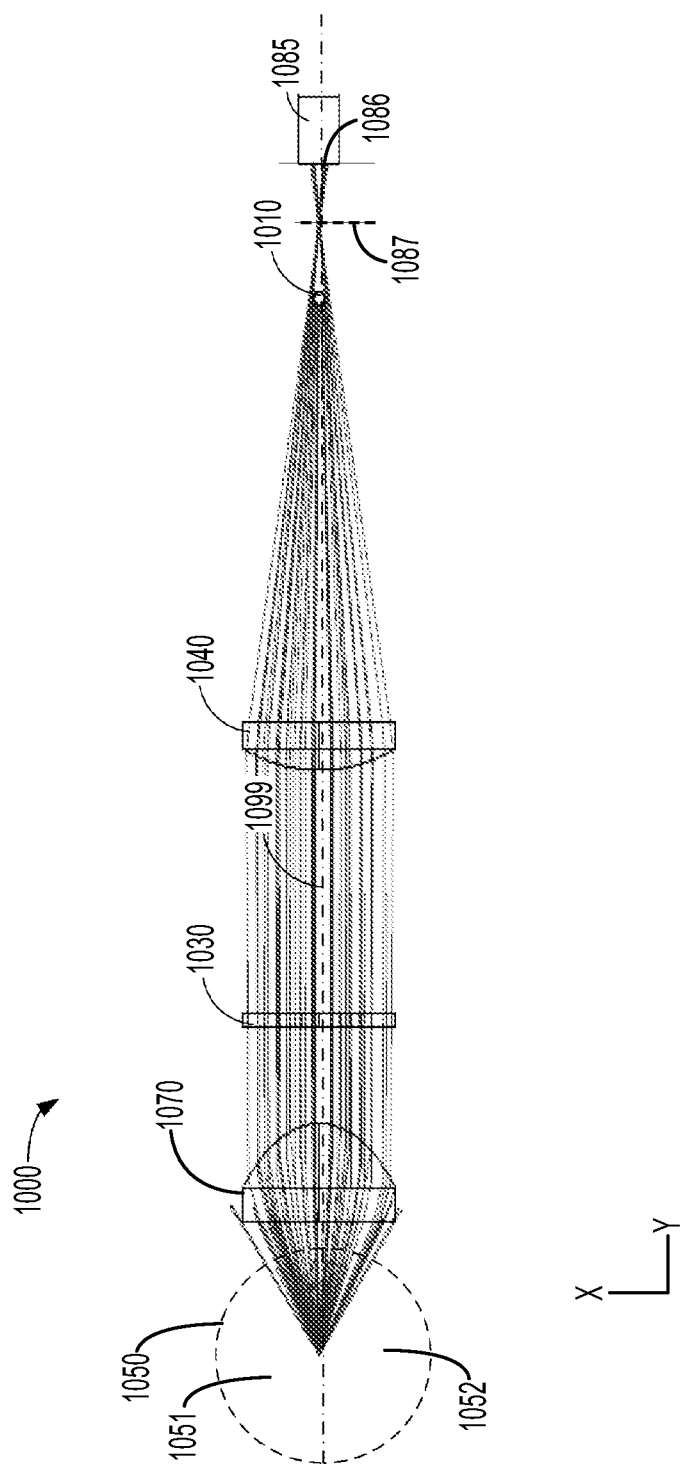
FIG. 10 is a top view of a ray tracing simulation of an optical system that includes an optical apparatus in accordance with some embodiments.

FIG. 9A illustrates the simulated performance of the split objective lens based on the model in FIG. 7 vs. the simulated performance of the comparative arrangement shown in FIG. 10 without the use of the spatial mask 1010. Graph 901 provides the intensity with respect to object position for a system that includes the split objective lens discussed above. Graph 902 is the intensity vs. position of the comparative arrangement and is provided in FIG. 9A for comparison. Note the higher overall collection efficiency of the split-objective arrangement in addition to the decreased effect of position variation on collected light intensity.

Figure 9B:
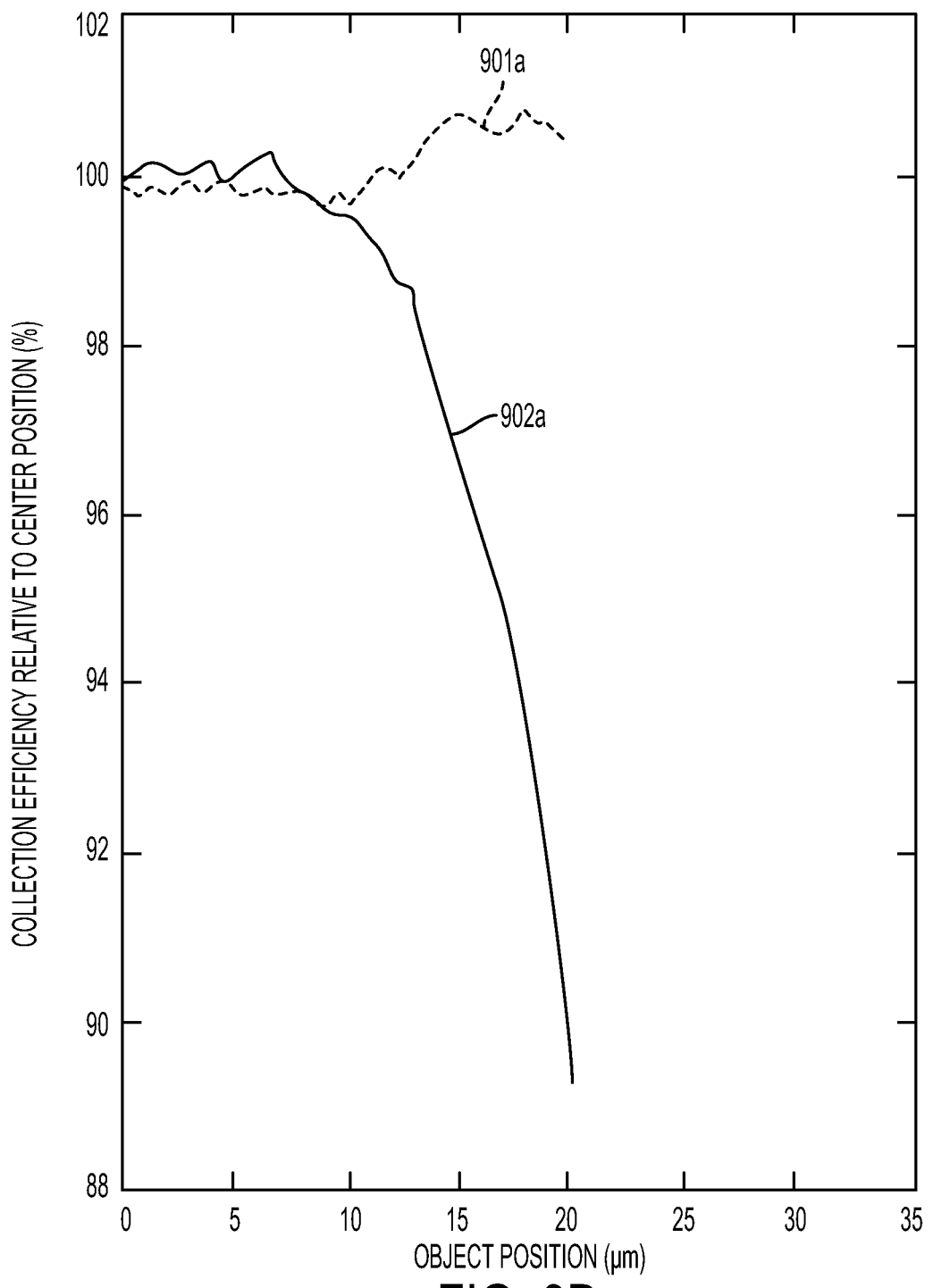

In order to show this comparison more clearly, in FIG. 9B, each graph 901a, 902a is normalized to 100%. Graph 901a provides the collection efficiency relative to center position for the split objective lens arrangement. Graph 902a shows the collection efficiency relative to center position for the comparative system with only a single objective lens. The split objective lens yields less than 1% deviation from the center collection efficiency at an object position of 20 μm, whereas the comparative arrangement yields over 10% deviation from the center collection efficiency at the same object position.

It is possible to decrease variation in the position vs. intensity profile using other approaches as well, all of which are considered novel aspects of the disclosure. For example, rather than a collection arrangement that selects rays in angle space (e.g., close to a pupil of the optical system), as exemplified by the split objective lens, it is possible to select rays in image or position space (e.g., close to an image plane of the optical system). One example of an optical collection arrangement that selects rays in position space is a spatial mask near an image plane of the optical system. In order to make such a mask easier to align and more robust to alignment, it helps to increase the optical system magnification, allowing one to use larger mask feature sizes.

FIG. 10 is a top view of a ray tracing simulation of an optical system 1000 that includes an optical collection arrangement 1010, e.g., a spatial mask, that attenuates light rays emanating from the object near the center of a flow stream cross section while not attenuating light rays emanating from the object at the top and bottom of the flow stream cross section. The term "attenuating" as used herein encompasses partially blocking or fully blocking the light rays. For example, an attenuated light ray may have an intensity reduction of 25% or 50% or 75% or even 100% when compared to its original intensity, wherein 25%, 50%, and 75% attenuation corresponds to a light ray that is partially blocked and 100% attenuation corresponds to a light ray that is fully blocked. The system 1000 shown in FIG. 10 includes a single objective lens 1070 that collimates light emanating from the object (object not shown in FIG. 10). System 1000 optionally includes a filter 1030, such as a bandpass filter or a longpass filter configured to block excitation light from reaching the detector 1085. A lens 1040 can be used to focus collected light toward the sensitive region 1086 of the detector 1085. A spatial mask 1010 attenuates or blocks light rays emanating from the center of the flow stream cross section 1050 from reaching the detector 1085 while not attenuating or blocking light rays emanating from the top and bottom regions 1051, 1052 of the flow stream cross section 1050 from reaching the detector 1085. In FIG. 10, the top region 1051 of the flow stream cross section 1050 refers to the portion of the flow stream cross section that is above the optical axis 1099 in FIG. 10. The bottom region 1052 of the flow stream cross section 1050 is below the optical axis 1099 in FIG. 10. The mask 1010 may be opaque to the emanating light or may be semi-transparent. In some embodiments, the optical optical transparency of the mask 1010 may vary with position, e.g., such that an image of the center of the flow stream cross section is more attenuated than an image of the top and/or bottom of the flow stream cross section.

A simple spatial mask that alleviates the variation in collected intensity with object position is a thin wire (for example, having a diameter in a range of about 100 microns to 300 microns, e.g., about 200 microns in diameter) in front of the optical detector 1085 and near an image of the flow stream, with the wire axis oriented parallel to the flow stream and nominally centered with respect to the optical axis 1099. The effect of the wire can be varied by moving it in and out of the image plane 1087, which is where an image of the flow stream appears (a magnified image in the current embodiment).

Figure 11:
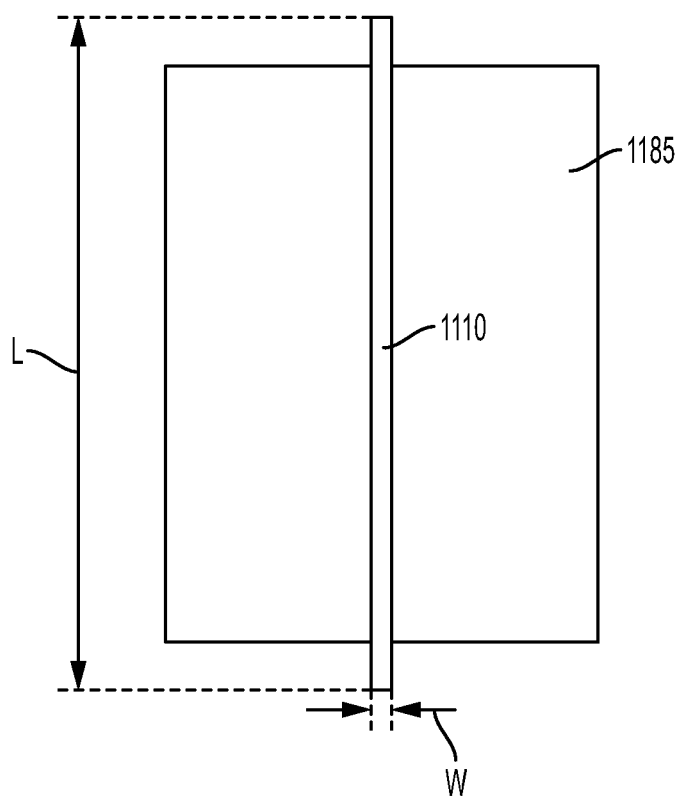
FIG. 11 illustrates an optical apparatus comprising an elongated mask feature in accordance with some embodiments.

A spatial mask that reduces the variation in collected intensity with object position is illustrated in FIG. 11. The spatial mask comprises an elongated feature 1110, which may be implemented as a thin wire having a circular cross sectional area, a bar having a rectangular cross sectional area or other mask feature disposed at least partially across the active area 1185 of the optical detector and near an image of the flow stream. The elongated mask feature 1110 can be implemented in many ways, including an extruded metal wire, an etched metal feature, human or animal hair, a trace deposited on a glass slide, or an ink line printed on a transparent medium.

Generally, the length of the mask feature, L, is much greater than its width, W. The mask feature 1110 may be oriented such that the length of the mask feature 1110 runs parallel to the flow stream and the mask feature 1110 is nominally centered with respect to the optical axis of the system (see FIG. 10). In some embodiments, the mask feature 1110 may have a width of about 100 microns to about 300 microns e.g., about 200 microns.

Figure 12:
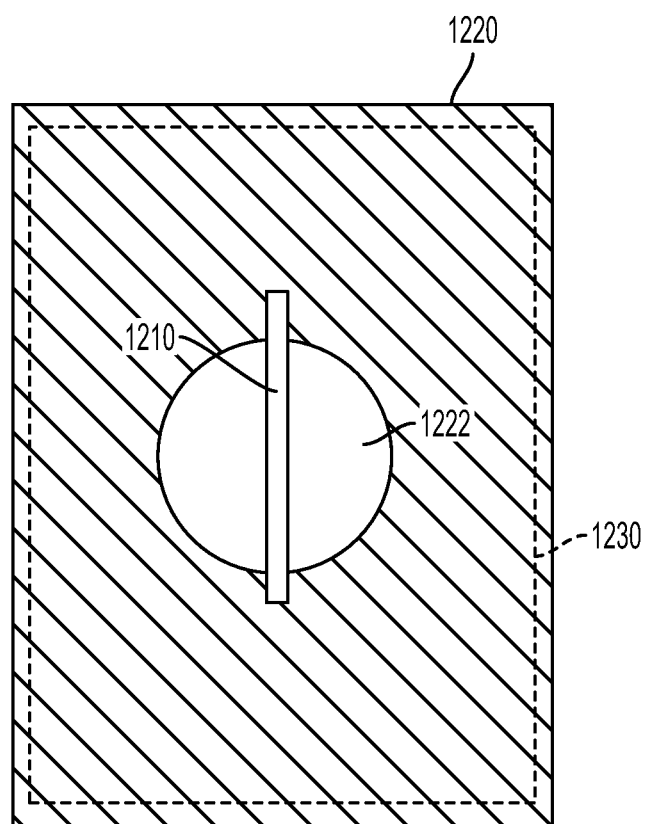
FIG. 12 depicts an optical apparatus comprising an elongated mask feature that can be used in conjunction with a plate having an aperture according to some embodiments.

As illustrated in FIG. 12, an elongated mask feature 1210 can be used in conjunction with a plate 1220 having an aperture 1222 wherein the elongated mask feature 1210 is disposed at least partially across the aperture 1222 as illustrated in FIG. 12. The plate 1220 can be particularly useful for alignment of the system optics to achieve the optimal intensity difference between objects of two types with slightly different intensities.

Figure 13:
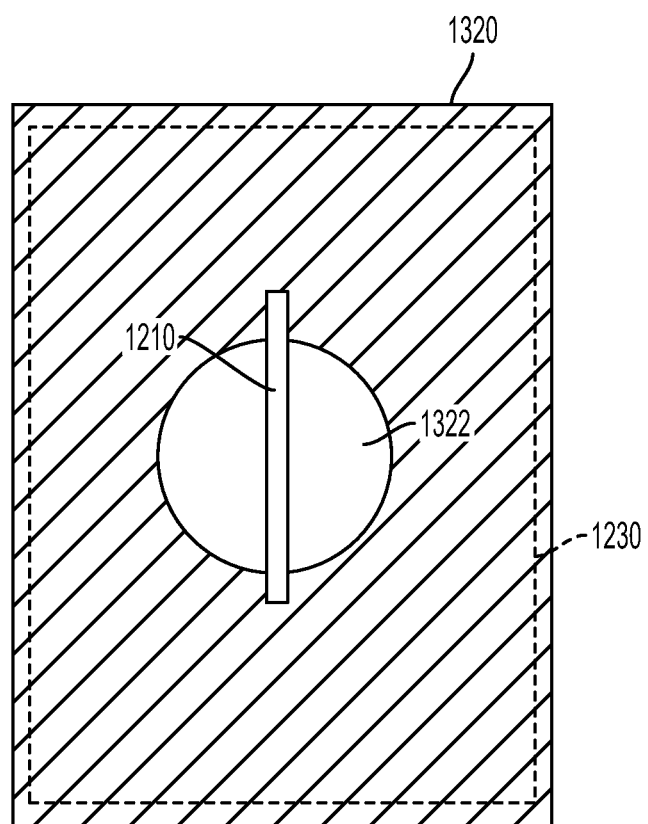
FIG. 13 illustrates an optical apparatus comprising a plate and elongated mask feature wherein the optical transparency of the plate varies smoothly with position in accordance with some embodiments.

In some embodiments, the plate may be made of a material that partially blocks (blocks more than 25% and less than 75% of the light), substantially blocks (blocks more than 75% of the light), or completely blocks (blocks 100% of the light) the light emanating from the object under test from reaching the active area 1230 of the detector. The aperture 1222 in the plate 1220 transmits substantially all of the light emanating from the object to the active area 1230 of the detector. The plate 1220 and aperture 1222 facilitates alignment of the system optics, allowing the operator to align the mask feature 1210 such that optimal contrast is achieved between the lower light intensity emanating from a first type of object and the slightly higher light intensity emanating from a second type of object FIG. 13 illustrates another embodiment in which the optical transparency of the plate varies across its length and width. In this example, the plate 1320 is more optically transparent closer to the aperture 1322 and is less transmissive farther from the aperture. However, the opposite scenario is also possible, wherein the plate is less transmissive near the aperture and more transmissive farther from the aperture.

Figure 14:
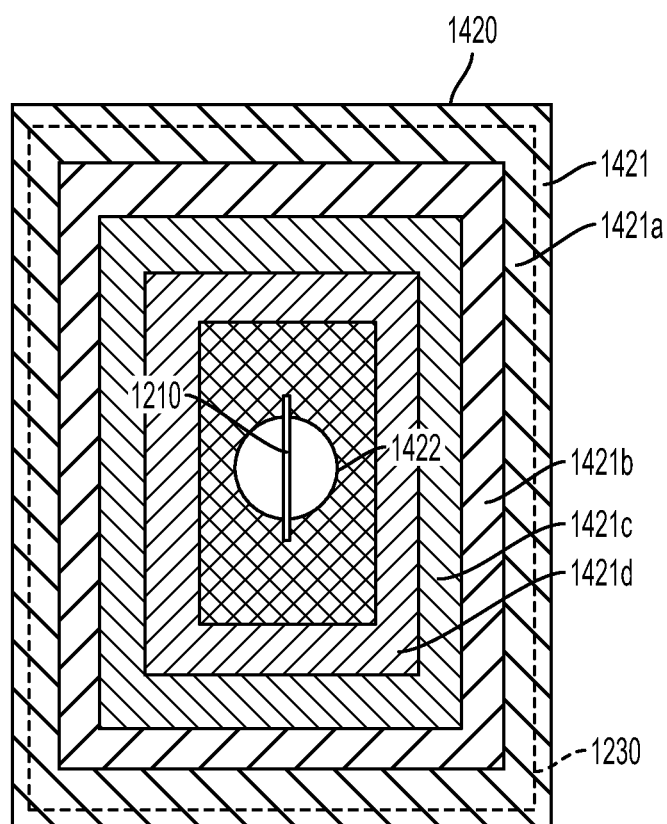
FIG. 14 illustrates an optical apparatus comprising a plate and elongated mask feature wherein the optical transparency of the plate varies with position in accordance with some embodiments.

FIG. 14 illustrates another version of a plate 1420 that has a stepwise optical transparency gradient. The plate 1420 becomes more optically transmissive closer to the aperture 1422 in distinct steps in regions 1421a, 1421b, 1421c, 1421d. Comparing the plate 1320 of FIG. 13 with the plate 1420 of FIG. 14, the optical transparency of plate 1320 makes a gradual transition from the outer edges of the plate 1320 having lower optical transparency transitioning to a higher optical transparency nearer the aperture 1322 in the center of the plate 1320.

Figure 15:
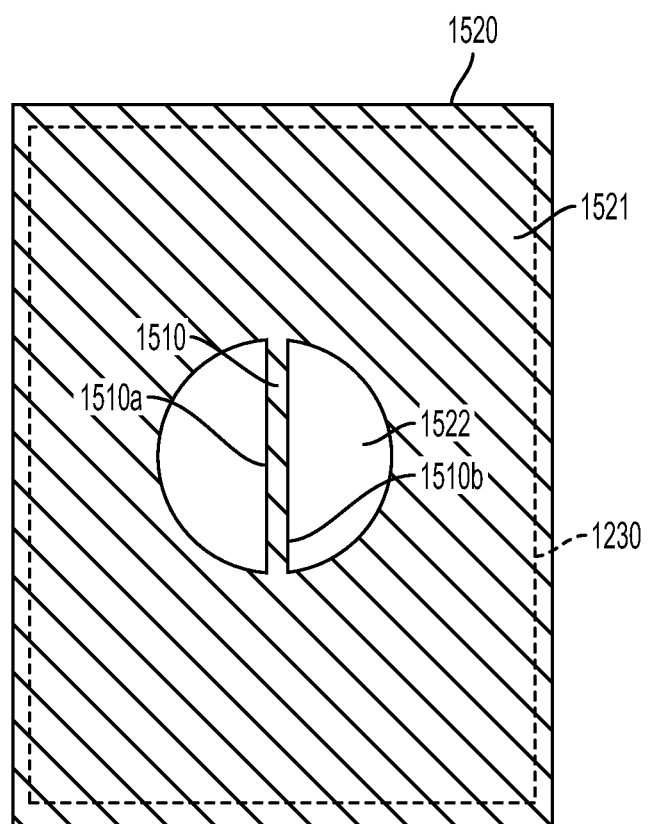
FIG. 15 is a diagram of an optical apparatus comprising plate and an elongated mask feature extending across an aperture formed as a unitary structure in accordance with some embodiments.

In some embodiments, the aperture plate and the elongated mask feature extending across the aperture are formed as a unitary structure as illustrated in FIG. 15. FIG. 15 shows a plate 1520 including an elongated feature 1510 that bisects the aperture 1522. In some embodiments the unitary aperture plate 1520 can have a optical transparency gradient as previously discussed and illustrated with reference to FIGS. 13 and 14. A unitary aperture plate as in FIG. 15 can be formed, for example, by photoetching a metal plate.

Figure 16:
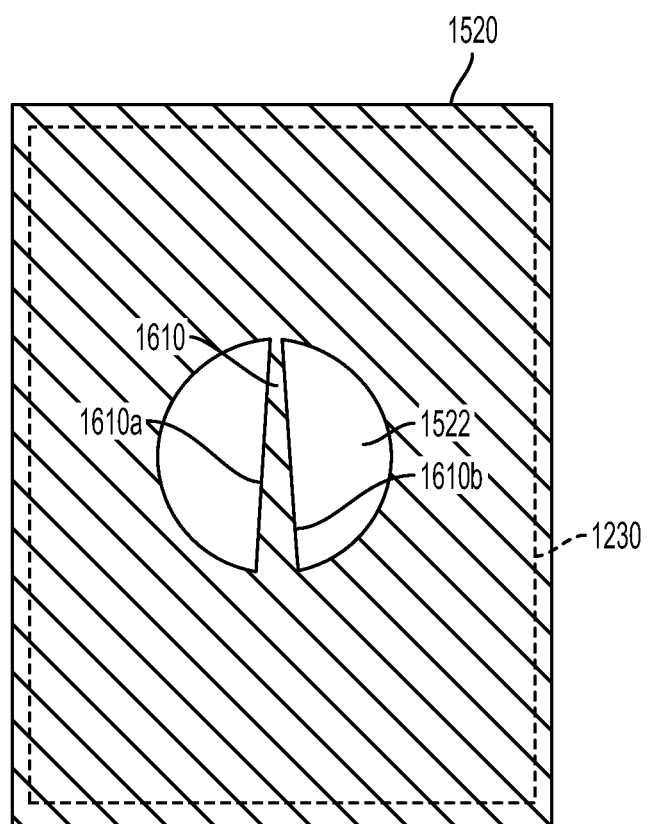
FIGS. 16 through 18 illustrate various configurations of longitudinal edges of elongated mask features in accordance with several embodiments.
Figure 17:
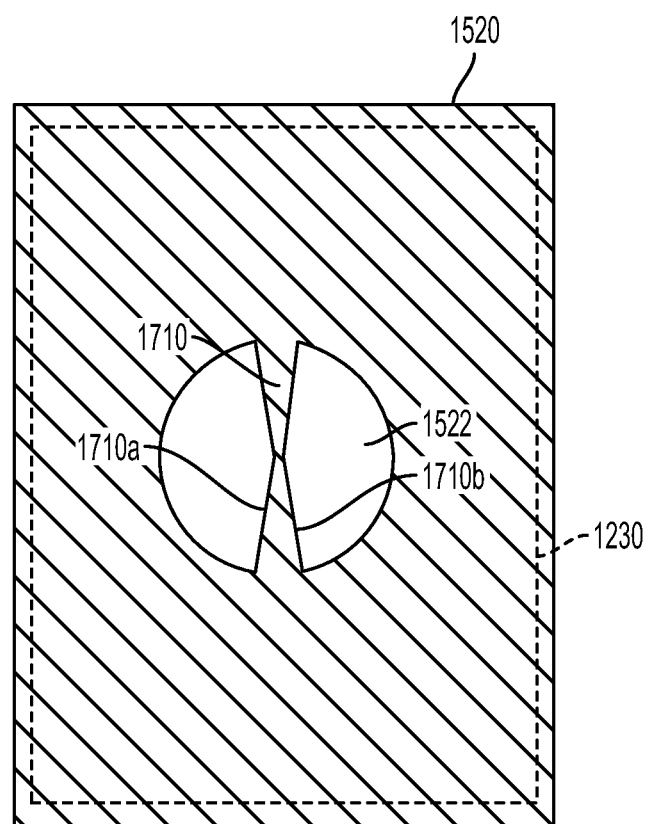
Figure 18:
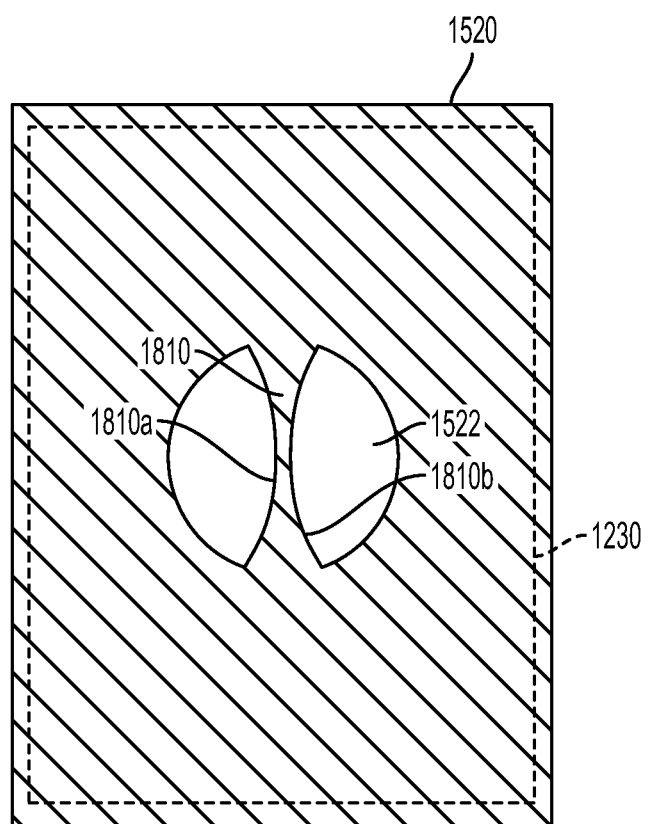

The longitudinal edges 1510a, 1510b of the elongated mask feature 1510 need not be parallel as they are shown in FIG. 15. In some embodiments the alignment process may be enhanced by having an elongated mask feature 1610, 1710 with non-parallel longitudinal edges 1610a, 1610b, 1710a, 1710b as shown in FIGS. 16 and 17. In some embodiments the longitudinal edges 1810a, 1810b of the elongated mask feature 1810 may be curved as illustrated in FIG. 18.

Figure 19:
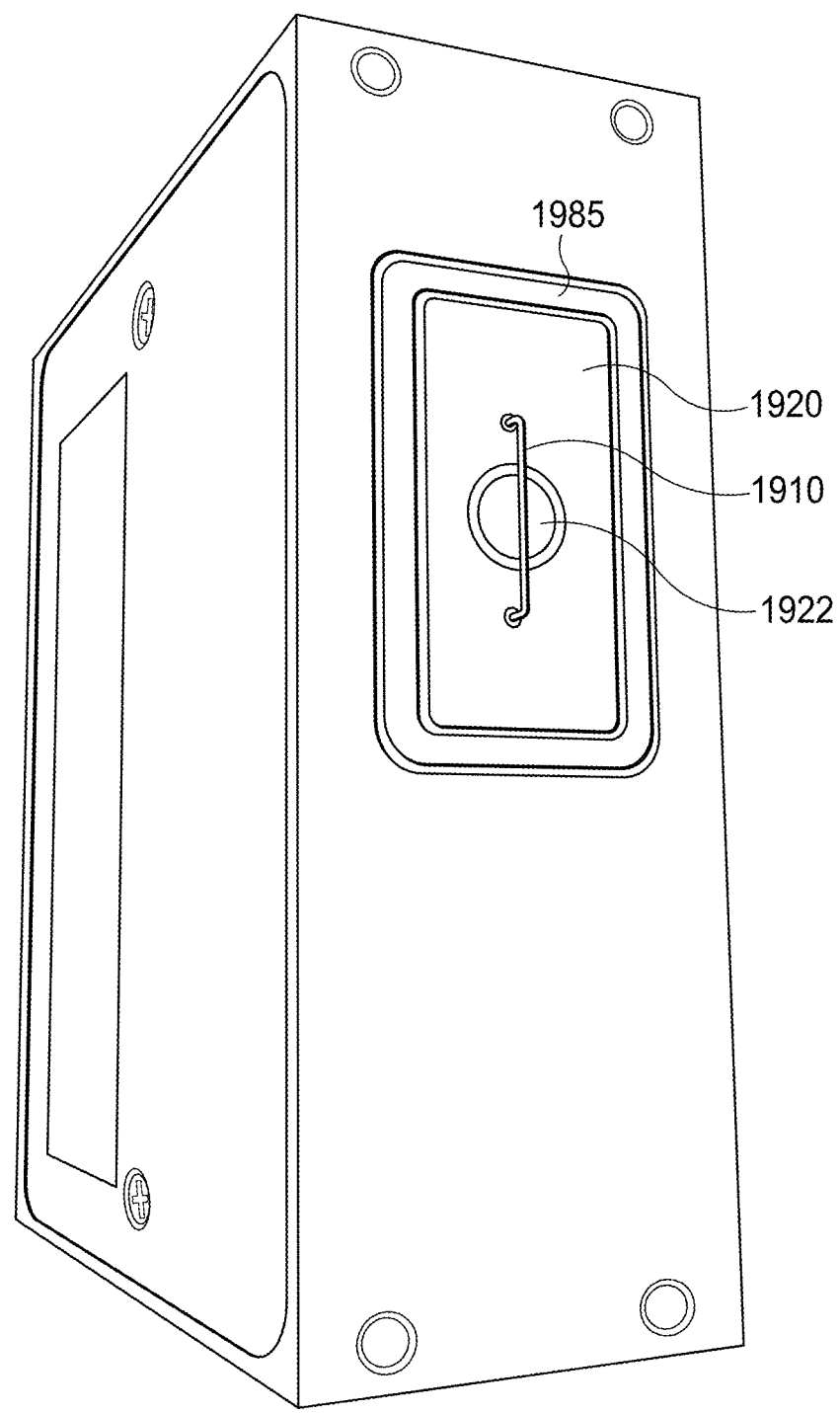
FIG. 19 is a photograph of an optical apparatus that includes a wire mask in accordance with some embodiments.

FIG. 19 is a photograph showing an optical arrangement comprising a plate 1920 having an aperture 1922 in accordance with some embodiments. An elongated mask feature 1910 comprising a thin wire is positioned across the aperture 1922 in front of the entrance to a photomultiplier tube detector. The wire modifies the output light emanating from objects in the flow stream by preferentially attenuating light emanating from objects at the center of the flow stream cross section as previously discussed. The preferential attenuation of light provides a more uniform light intensity vs. object position profile when compared to the unmodified output light.

Figure 20:
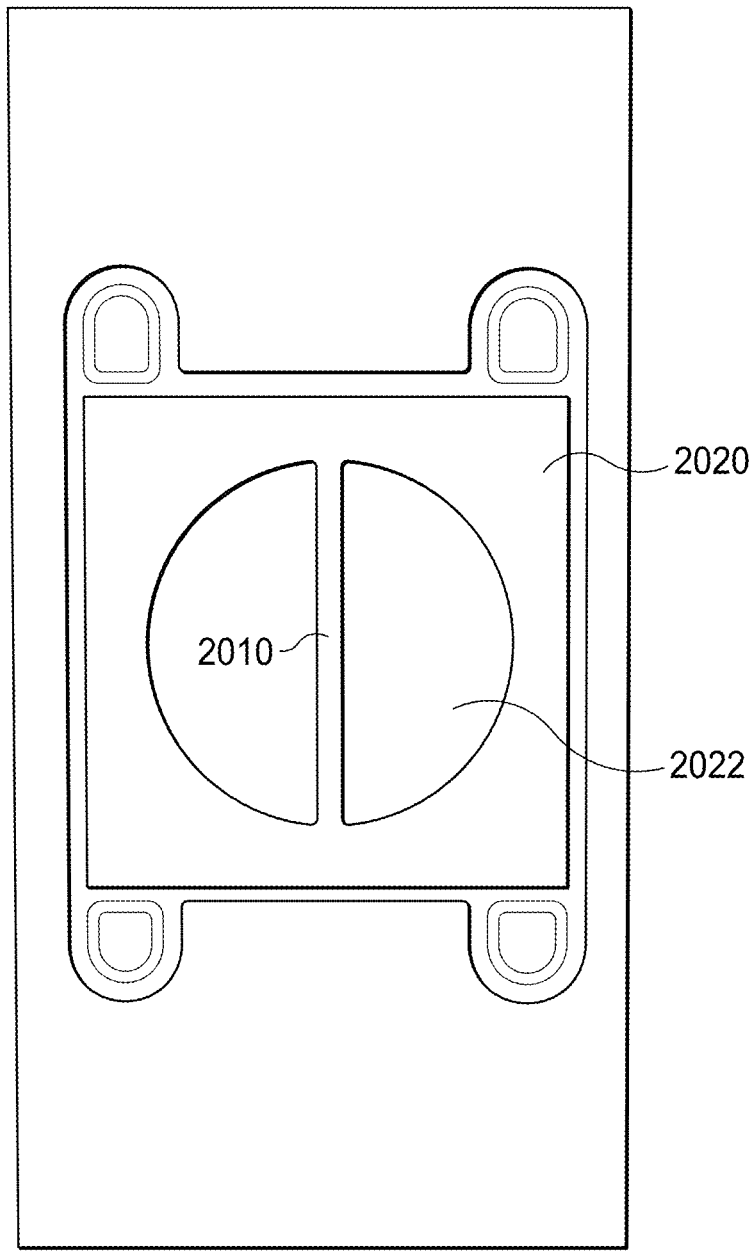
FIG. 20 is a photograph of an optical apparatus that includes a plate having an elongated mask feature extending across an aperture formed as a unitary structure in accordance with some embodiments.

FIG. 20 is photograph showing an optical arrangement in accordance with some embodiments comprising a plate 2020 and elongated mask feature 2010 extending across an aperture 2022 formed as one unitary structure. For example, the plate and elongated mask feature 2010 may be formed by photoetching the (split) aperture 2022.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. A discrimination system, comprising:
    an excitation light source configured to generate excitation light and to direct the excitation light toward an object in a fluid column having a center, the object emanating output light in response to the excitation light;
    a detector having an aperture for collecting the output light and to provide an electrical signal in response;
    an elongated mask feature located across the aperture of the detector for modifying the output light wherein the elongated mask feature is disposed at about a center of the aperture of the detector to preferentially attenuate output light received by the detector from the center of the fluid column; and
    object type discrimination circuitry configured to discriminate between a first type of object and a second type of object based on the electrical signal.

2. The system of claim 1, wherein the intensity of the modified output light is substantially uniform irrespective of a position of the object within the fluid column.

3. The system of claim 1, wherein the object type discrimination circuitry is configured to perform X/Y sperm cell discrimination.

4. The system of claim 1, wherein the elongated mask feature preferentially attenuates output light received from a first position in the fluid column compared to output light received from a second position in the fluid column, wherein the second position is farther from the center of the fluid column than the first position along an axis perpendicular to an optical axis of the detector.

5. The system of claim 4, wherein the elongated mask feature has a round cross sectional area.

6. The system of claim 4, wherein the elongated mask feature has a rectangular cross sectional area.

7. The system of claim 4, wherein the elongated mask feature comprises a metal wire.

8. The system of claim 4, wherein the elongated mask feature comprises a trace deposited on glass.

9. The system of claim 4, wherein the elongated mask feature comprises a filament.

10. The system of claim 4, wherein the elongated mask feature comprises an ink line printed on transparent paper.

* * * * *